US012616739B2

(12) United States Patent
Lau et al.

(10) Patent No.: US 12,616,739 B2
(45) Date of Patent: May 5, 2026

(54) GLP-1 PRODRUGS AND USES THEREOF

(71) Applicant: Novo Nordisk A/S, Bagsvaerd (DK)

(72) Inventors: Jesper F. Lau, Farum (DK); Lennart Lykke, Koebenhavn V (DK); Bhavesh Premdjee, Frederiksberg (DK); Cecilie Mia Joergensen, London (GB)

(73) Assignee: Novo Nordisk A/S, Bagsvaerd (DK)

( * ) Notice: Subject to any disclaimer, the term of this patent is extended or adjusted under 35 U.S.C. 154(b) by 557 days.

(21) Appl. No.: 18/034,761

(22) PCT Filed: Nov. 5, 2021

(86) PCT No.: PCT/EP2021/080747
§ 371 (c)(1),
(2) Date: May 1, 2023

(87) PCT Pub. No.: WO2022/096636
PCT Pub. Date: May 12, 2022

(65) Prior Publication Data

US 2025/0268986 A1 Aug. 28, 2025

(30) Foreign Application Priority Data

Nov. 6, 2020 (EP) .................................... 20206198
Jun. 29, 2021 (EP) .................................... 21182351

(51) Int. Cl.

| | |
|---|---|
| ***A61K 38/00*** | (2006.01) |
| ***A61K 38/26*** | (2006.01) |
| ***A61K 47/54*** | (2017.01) |
| ***C07K 14/605*** | (2006.01) |

(52) U.S. Cl.
CPC ........... *A61K 38/26* (2013.01); *A61K 47/542* (2017.08); *C07K 14/605* (2013.01)

(58) Field of Classification Search
None
See application file for complete search history.

(56) References Cited

FOREIGN PATENT DOCUMENTS

| | | | | | |
|---|---|---|---|---|---|
| WO | 99043706 | A1 | | 9/1999 | |
| WO | 2006097537 | | | 9/2006 | |
| WO | 2010/029159 | A1 | | 3/2010 | |
| WO | 2010071807 | A1 | | 6/2010 | |
| WO | 10080605 | A1 | | 7/2010 | |
| WO | 2010/102886 | A1 | | 9/2010 | |
| WO | 11073328 | A1 | | 6/2011 | |
| WO | 2011/080102 | A2 | | 7/2011 | |
| WO | 2011080103 | A1 | | 7/2011 | |
| WO | 2011089216 | A1 | | 7/2011 | |
| WO | 11163012 | A2 | | 12/2011 | |
| WO | 2012062803 | A1 | | 5/2012 | |
| WO | 13127779 | A1 | | 9/2013 | |
| WO | WO-2013127779 | A1 | * | 9/2013 | ............. A61P 43/00 |
| WO | 2014152460 | A2 | | 9/2014 | |
| WO | 2016049174 | A1 | | 3/2016 | |
| WO | 18083335 | A1 | | 5/2018 | |
| WO | 2019149880 | A1 | | 8/2019 | |
| WO | 2019229242 | A1 | | 12/2019 | |

OTHER PUBLICATIONS

Arnab De et al., "Investigation of the Feasibility of an Amide-based Prodrug Under Physiological Conditions," International Journal of Peptide Research and Therapeutics, Aug. 2008, vol. 14, No. 3, pp. 255-262.

Hodgson et al., "The Synthesis of Peptides and Proteins Containing Non-Natural Amino Acids", Chemical Society Reviews, Oct. 2004, vol. 33, No. 7, pp. 422-430.

Lau et al., "Discovery of the Once-Weekly Glucagon-Like Peptide?1 (GLP-1) Analogue Semaglutide," J. Med. Chem., 2015, vol. 58, pp. 7370-7380.

Myers et al., "Optimal alignments in linear space", CABIOS, Mar. 1988, vol. 4, No. 1, pp. 11-17.

Needleman et al., "A general method applicable to the search for similarities in the amino acid sequence of two proteins", Journal of Molecular Biology, Mar. 1970, vol. 48, No. 3, pp. 443-453.

* cited by examiner

*Primary Examiner* — Lianko G Garyu
*Assistant Examiner* — Mercy H Sabila
(74) *Attorney, Agent, or Firm* — Jianjie Hu

(57) ABSTRACT

The invention relates to DKP-based prodrugs. The invention also relates to the use of DKP-based prodrugs.

24 Claims, 1 Drawing Sheet

Specification includes a Sequence Listing.

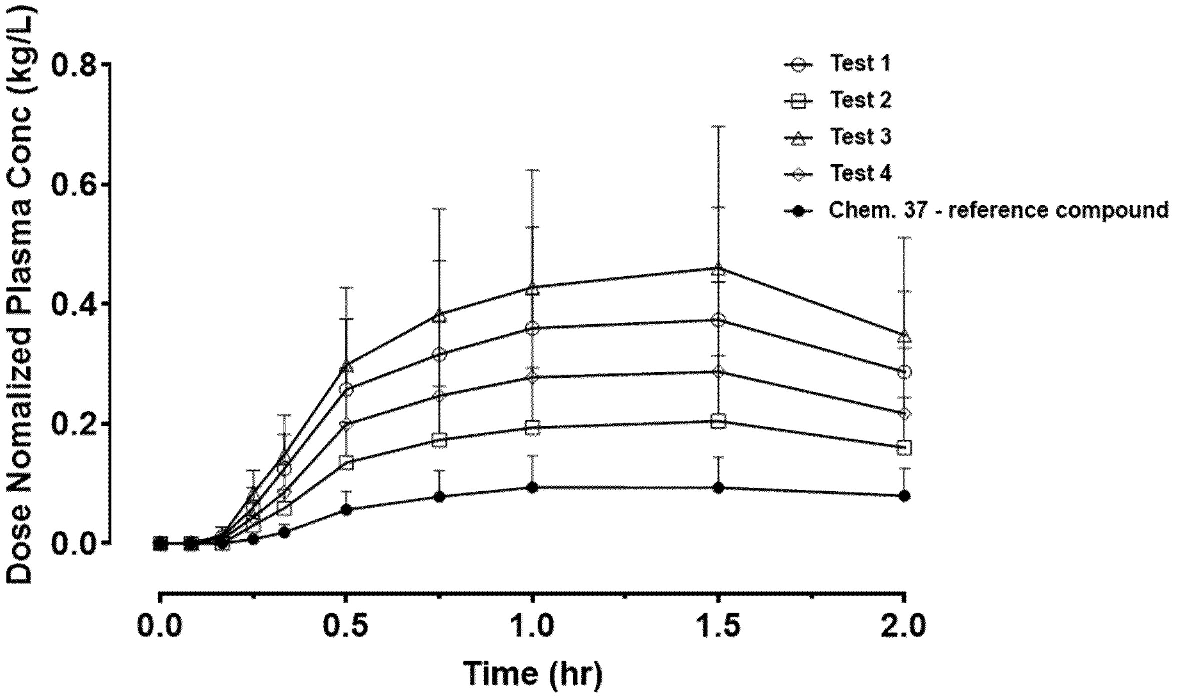
Dose Nomalized Plasma Conc (kg/L)
0.8
0.6
0.4
0.2
0.0
0.0
0.5
1.0
1.5
2.0
Time (hr)
Test 1
Test 2
Test 3
Test 4
Chem. 37 - reference compound

GLP-1 PRODRUGS AND USES THEREOF

CROSS-REFERENCE TO RELATED APPLICATIONS

This application is a 35 U.S.C. § 371 National Stage application of International Application PCT/EP2021/080747 (WO2022/096636), filed Nov. 5, 2021, which claims priority to European Patent Application 20206198.2, filed Nov. 6, 2020 and European Patent Application 21182351.3, filed Jun. 29, 2021; the contents of which are incorporated herein by reference.

INCORPORATION-BY-REFERENCE OF THE SEQUENCE LISTING

A computer-readable form of the sequence listing was indicated on the PCT Request as part of the International Application No. PCT/EP2021/080747 and the sequence listing was published as part of the International application. Thus, in accordance with PCT Rule 13ter.3 and 37 CFR 1.821-1.825, the sequence listing is not submitted herewith.

TECHNICAL FIELD

The invention relates to DKP-based prodrugs as well as the therapeutic use thereof.

SEQUENCE LISTING

The present application is filed with a Sequence Listing in electronic form. The entire content of the sequence listing is hereby incorporated by reference.

BACKGROUND

Prodrug technology may be used to generate compounds with properties suitable for a specific dosing frequency. Diketopiperazine (DKP) based prodrugs has previously been described (e.g. Arnab De, Richard D. DiMarchi, Investigation of the Feasibility of an Amide-based Prodrug Under Physiological Conditions, *International Journal of Peptide Research and Therapeutics,* 2008, Vol 14, 3, pp 255-262). This technology is based on a chemical conversion where a moiety consisting of two amino acids cyclize to form a six membered ring whereupon the active drug is liberated.

- WO2010/071807 allegedly discloses prodrug formulations of glucagon superfamily peptides wherein the peptide has been modified by linkage of a dipeptide through an amide bond linkage.
- WO2010/080605 allegedly discloses a non-enzymatically self-cleaving dipeptide element linked to known medical agents via an amide bond
- WO2011/163012 allegedly discloses prodrug formulations of glucagon superfamily peptides wherein the peptide has been modified by linkage of a dipeptide through an amide bond linkage.
- WO2013/127779 allegedly discloses ester prodrugs of insulinotropic peptides.
- WO2014/152460 allegedly discloses peptide-based prodrugs having significantly extended half-lives.
- WO2016/049174 allegedly discloses prodrug formulations of insulin and insulin analogues wherein the insulin peptide has been modified by an amide bond linkage of a dipeptide prodrug element.

- WO2011/089216 allegedly discloses dipeptide-based prodrugs for aliphatic amine-containing drugs.

SUMMARY

GLP-1 receptor agonists are widely used for treatment of chronic disease. Currently available oral GLP-1 receptor agonist medicaments must be administered once daily. A treatment regimen with less frequent dosing than once daily may lead to improved patient convenience and improved patient compliance, and consequently the development of oral GLP-1 receptor agonists suitable for dosing less frequently than once daily would constitute a significant improvement to the available treatment options. Prodrug technology may be employed to optimise the properties of a drug in a manner that makes it suitable for a specific dosing regimen, e.g. for once weekly dosing. The present invention relates to prodrugs with desirable properties, e.g. for once weekly oral dosing.

In a first aspect the invention relates to a compound comprising Formula I: A-Z; wherein Z comprises a GLP-1 polypeptide, and wherein A is of Formula II:

(Formula II)

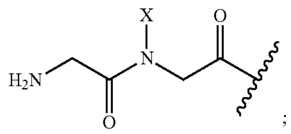

;

wherein X is of Formula III:

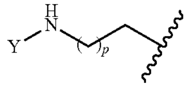

wherein p=1-5 (Formula III);

wherein Y comprises a lipophilic moiety with a distal carboxylic acid; or a pharmaceutical acceptable salt, ester or amide thereof.

In a second aspect the invention relates to the prodrug of the invention for use as a medicament. In one functional aspect the invention provides for a prodrug that has a conversion half-life suitable for once-weekly dosing. Also or alternatively, in a another functional aspect the invention provides for a prodrug that has an observed terminal half-life suitable for once-weekly dosing. Also or alternatively, in another functional aspect the invention provides for a prodrug that has a surprisingly high oral bioavailability. The invention may also solve further problems that will be apparent from the disclosure of the exemplary embodiments.

BRIEF DESCRIPTION OF DRAWINGS

FIG. 1: Dose normalised plasma concentration (vs time) profiles of test compound following oral administration in Beagle dogs.

DESCRIPTION

In what follows, Greek letters may be represented by their symbol or the corresponding written name, e.g.: α=alpha; β=beta; ε=epsilon; γ=gamma; ω=omega; etc. Also, the Greek letter of μ may be represented by "u", e.g. in μl=ul, or in µM=uM. The symbol * in a chemical formula or in a chemical drawing designates a point of attachment to a neighbouring moiety. In what follows, unless otherwise indicated in the specification, terms presented in singular form also include the plural situation, e.g. when referring to the "compound", it is to be understood that this embraces all individual variants falling within a broad definition of said compound.

The present invention relates to prodrugs with desirable properties, e.g. for once weekly oral dosing. In a first aspect the invention relates to a prodrug comprising Formula I: A-Z, wherein Z is a parent drug that is liberated from A upon conversion of the prodrug. In a second aspect the invention relates to the prodrug of the invention for use as a medicament.

General Definitions

The term "compound" as used herein refers to a molecular entity, and "compounds" may thus have different structural elements besides the minimum element defined for each compound or group of compounds. The term compound is used interchangeably with the term "construct". The term "compound" may be used to describe a prodrug of the invention. The compounds of the invention may be referred to as "compound", and the term "compound" is also meant to cover pharmaceutically relevant forms hereof, i.e. the invention relates to a compound as defined herein or a pharmaceutically acceptable salt, amide, or ester thereof.

The term "polypeptide" or "polypeptide sequence", as used herein refers to a compound which comprises a series of two or more amino acids interconnected via amide (or peptide) bonds. The term polypeptide is used interchangeably with the term "peptide" and the term "protein".

The term "analogue" as used herein generally refers to a polypeptide, the sequence of which has one or more amino acid changes as compared to a reference amino acid sequence.

Said amino acid changes may include amino acid additions, amino acid deletions, and/or amino acid substitutions. Amino acid substitutions, deletions and/or additions may also be referred to as "mutations". In particular embodiments, an analogue "comprises" specified changes. In other particular embodiments, an analogue "consists of" or "has" specified changes. When the term "comprises" or "comprising" is used in relation to amino acid changes in an analogue, it should be understood that the analogue may have further amino acid changes as compared to its reference sequence. When the term "consisting of" or "has" is used in relation to amino acid changes in an analogue, it should be understood that the specified amino acid mutations are the only amino acid changes in the analogue as compared to the reference sequence.

The term "derivative" generally refers to a chemically modified polypeptide in which one or more substituents are covalently linked to the amino acid sequence of the polypeptide, e.g. via a bond to the ε-amino group of a Lys. In one embodiment, the compound of the invention comprises a derivative, which has been modified so that one or more substituents with protracting properties are covalently linked to the amino acid sequence of the polypeptide.

The term "sequence identity" as used herein refers to the extent to which two amino acid sequences (e.g. polypeptides) have the same residues at the same positions in an alignment. This may also be referred to merely as "identity". The sequence identity is conveniently expressed as a percentage, i.e. if 85 amino acids out of 100 aligned positions between the two sequences are identical the degree of identity is 85%. For purposes of the present invention, the sequence identity between two amino acid sequences is determined by using simple handwriting and eyeballing; and/or a standard protein or peptide alignment program, such as "align" which is based on a Needleman-Wunsch algorithm. This algorithm is described in Needleman, S. B. and Wunsch, C. D., (1970), Journal of Molecular Biology, 48:443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.

Amino Acids

The term "amino acid" as used herein refers to any amino acid, i.e. both proteinogenic amino acids and non-proteinogenic amino acids. The term "proteinogenic amino acids" as used herein refers to the 20 standard amino acids encoded by the genetic code in humans. The term "non-proteinogenic amino acids" as used herein refers to any amino acid which does not qualify as a proteinogenic amino acid. In general, amino acid residues, e.g. in context of a polypeptide sequence, as used herein, may be identified by their full name, their one-letter code, and/or their three-letter code. These three ways are fully equivalent and used interchangeably. In what follows, each amino acid of the peptides of the invention for which the optical isomer is not stated is to be understood to mean the L-isomer (unless otherwise specified).

GLP-1 Polypeptide

The term "GLP-1 polypeptide" as used herein refers to a polypeptide which is capable of binding to a GLP-1 receptor and/or to activating a GLP-1 receptor. In other words, a GLP-1 polypeptide is a polypeptide which has GLP-1 activity. In other words, a GLP-1 polypeptide is a GLP-1 receptor agonist. A GLP-1 polypeptide may bind to and/or activate other types of receptors, i.e. as long as the polypeptide binds and/or activates the GLP-1 receptor it qualifies as a GLP-1 polypeptide regardless of any other receptor interactions it may be associated with. In addition to amino acid residues responsible for the GLP-1 receptor interaction, the GLP-1 polypeptide may contain further amino acid residues which are not involved in the GLP-1 receptor interaction.

The term "GLP-1 receptor agonist" as used herein refers to a compound which is capable of binding to a GLP-1 receptor and/or to activating a GLP-1 receptor. A GLP-1 receptor agonist is said to have "GLP-1 activity". A GLP-1 receptor agonist may be based on any type of molecular scaffold, e.g. a small molecule, a polypeptide and an antibody, or any combination hereof. A GLP-1 receptor agonist may comprise one or more moieties which are capable of activating the GLP-1 receptor.

The term "GLP-1 analogue" as used herein refers to an analogue (or variant) of the human glucagon-like peptide-1 (GLP-1 (7-37)). The amino acid sequence of human GLP-1 (7-37) is included in the sequence listing as SEQ ID NO: 1. The amino acid sequence of a GLP-1 analogue has one or more amino acid changes as compared to GLP-1 (7-37). Said amino acid changes may include amino acid additions, amino acid deletions, and/or amino acid substitutions. The amino acid sequence of semaglutide is a non-limiting example of a GLP-1 analogue.

The term "GLP-1 derivative" as used herein refers to a chemically modified GLP-1 polypeptide, in which one or more substituents have been covalently attached to the GLP-1 polypeptide. For example, a GLP-1 derivative is a GLP-1 analogue to which one or more substituents are covalently linked. A non-limiting example of a GLP-1 derivative is semaglutide.

In one embodiment, the compound of the invention comprises a GLP-1 polypeptide. In one embodiment, the GLP-1 polypeptide is the amino acid sequence of semaglutide. In one embodiment the compound of the invention comprises a GLP-1 polypeptide, wherein the GLP-1 polypeptide is a GLP-1 analogue, and wherein the GLP-1 analogue has maximum of 3 amino acid changes as compared to GLP-1 (7-37) (SEQ ID NO: 1). In one embodiment the compound of the invention comprises a GLP-1 polypeptide, wherein the GLP-1 polypeptide is a GLP-1 analogue, and wherein the GLP-1 analogue has maximum of 2 amino acid changes as compared to GLP-1 (7-37) (SEQ ID NO: 1). In one embodiment, the compound of the invention comprises a GLP-1 derivative. In one embodiment, the GLP-1 polypeptide is semaglutide.

Substituent

The term “substituent”, as used herein, refers to a moiety that is covalently attached to a polypeptide, e.g. attached to a GLP-1 polypeptide or to a dipeptide extension of a GLP-1 polypeptide such as the dipeptide extension that is present in the compounds of the invention, thus forming part of a DKP moiety. If a substituent is attached to a polypeptide or a dipeptide, the polypeptide or the dipeptide is said to be “substituted”. When a substituent is covalently attached to a polypeptide or to an amino acid residue, said polypeptide or amino acid is said to “carry” a substituent. The substituent may comprise a series of individually defined moieties; these moieties may be referred to as “substituent elements”.

The substituent may be capable of forming non-covalent binding with albumin, thereby promoting the circulation of the compound in the blood stream, and thus having the effect of protracting the time of which the compound is present in the blood stream, since the aggregate of the fusion compound and albumin is only slowly disintegrated to release the free form of the compound; thus, the substituent, as a whole, may also be referred to as an “albumin-binding moiety”, and the substituent may be said to have a “protracting effect”. The substituent may comprise a portion which is particularly relevant for the albumin binding and thereby the protraction, which portion may be referred to as a “protractor” or a “protracting moiety”. The substituent may be a lipophilic moiety with a distal carboxylic acid.

The substituent may comprise a portion between the protracting moiety and the point of attachment to the polypeptide, which portion may be referred to as a “linker”. The linker may comprise several “linker elements”. The linker elements may be selected so that they improve the overall properties of the molecule, e.g. so that they improve the oral bioavailability, the conversion half-life or the protracting effect, thus improving the overall exposure profile upon oral administration of the compound.

The nomenclature used to describe protracting moieties and linkers is as usual in the art, for example *—CO—* refers to carbonyl, —CH2- refers to methylene, and —COOH refers to carboxylic acid. Non-limiting examples of substituent elements are listed in Table 1.

TABLE 1

Non-limiting examples of substituent elements

| Reference | Structure |
|---|---|
| Chem. 1 | 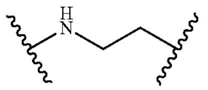 [SMILES: *CCN*] |
| Chem. 2 | 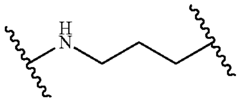 [SMILES: *CCCN*] |
| Chem. 3 | 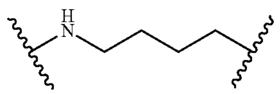 [SMILES: *CCCCN*] |
| Chem. 4 | 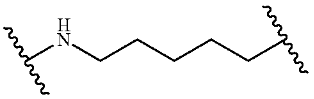 [SMILES: *CCCCCN*] |
| Chem. 5 | 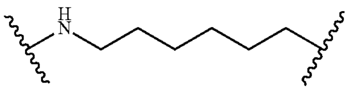 [SMILES: *CCCCCCN*] |
| Chem. 6 | 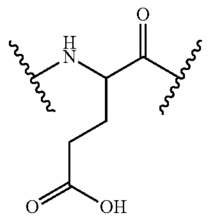 [SMILES: *NC(CCC(=O)O)C(*)=O] |
| Chem. 7 | 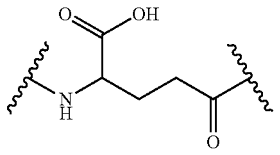 [SMILES: *NC(CCC(*)=O)C(=O)O] |
| Chem. 8 | 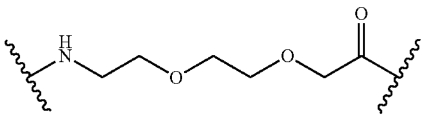 [SMILES: *NCCOCCOCC(*)=O] |
| Chem. 9 | 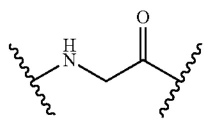 [SMILES: *NCC(*)=O] |
| Chem. 10 | 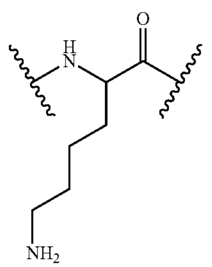 [SMILES: *NC(CCCCN)C(*)=O] |

TABLE 1-continued

| Non-limiting examples of substituent elements | |
|---|---|
| Reference | Structure |
| Chem. 11 | 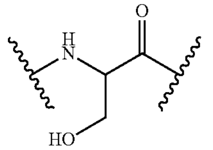 [SMILES: *NC(CO)C(*)=O] |
| Chem. 12 | 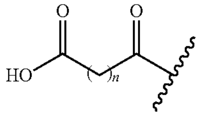 wherein n = 12, 14, 16 or 18 |
| Chem. 13 | 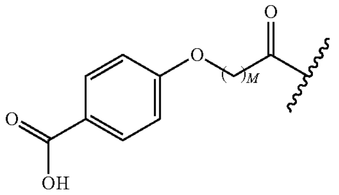 wherein m = 9 or 10 |

The term "lipophilic moiety" as used herein, refers to a moiety that comprises an aliphatic and/or a cyclic hydrocarbon moiety with a total of more than 6 and less than 30 carbon atoms, preferably more than 6 and less than 20 carbon atoms. The term "distal carboxylic acid" as used herein in context of the lipophilic moiety, refers to a carboxylic acid attached to the most remote (terminal) point of the lipophilic moiety relative to the lipophilic moiety's point of attachment to adjacent moieties, e.g. in the compounds of the invention, the lipophilic moiety with distal carboxylic acid (e.g. Chem. 12 and Chem. 13) is a protracting moiety, and the carboxylic acid is attached to the most remote (terminal) point of the lipophilic moiety relative to the lipophilic moiety's point of attachment to the adjacent linker elements (e.g. 10 Chem. 6, Chem. 7). Non-limiting examples of a lipophilic moiety with distal carboxylic acid are Chem. 12 and Chem. 13.

In one embodiment the compounds of the invention comprises a substituent. In one embodiment the substituent comprises a lipophilic moiety with distal carboxylic acid. In one embodiment, the lipophilic moiety with distal carboxylic acid is selected from a group consisting of Chem. 12 and Chem. 13. In one embodiment the substituent comprises a moiety selected from a group consisting of Chem. 6 and Chem. 7. In one embodiment the substituent comprises a moiety which is of Formula IV: $A_5$-$A_4$-$A_3$-$A_2$-$A_1$- (Formula IV); wherein $A_1$, $A_2$ and $A_3$ are each individually selected from a group consisting of Chem. 6, Chem. 7, Chem. 8, Chem. 9, Chem. 10, and Chem. 11, or is absent; wherein $A_4$ is selected from a group consisting of Chem. 6 and Chem. 7; wherein $A_5$ is selected from the group consisting of Chem. 12 and Chem. 13. In one embodiment the residues $A_5$, $A_4$, $A_3$, $A_2$, $A_1$ are interconnected via amide bonds.

Prodrug

The term "prodrug" as used herein refers to a compound that undergoes chemical conversion by an enzymatic or a non-enzymatic chemical process in vivo resulting in liberation of a parent drug. The term "parent drug" as used herein refers to pharmacological active compound which is liberated from a prodrug upon conversion of the prodrug. The term "conversion" as used herein in context of a prodrug refers to a process wherein the prodrug is converted in an enzymatic or a non-enzymatic manner resulting in the liberation of a parent drug. The rate with which the conversion takes place may be quantified by the "conversion half-life". The "conversion half-life" is the length of time required for the concentration of the prodrug to be reduced to half as a consequence of conversion. The "conversion half-life" may also be referred to as the "prodrug to drug conversion half-life" or as "prodrug to parent drug conversion half-life".

The intact prodrug is not exerting the intended pharmacological activity to a significant extent, e.g. it is not exerting the intended pharmacological activity to an extent that makes it incompatible with the treatment regime it is intended for. The pharmacological activity associated with the intended treatment of the prodrug is derived from the parent drug once it is liberated. When the parent drug is liberated from the prodrug is it said to be in its "free form". The prodrug may achieve the desired conversion upon intramolecular cyclization of a terminal dipeptide-based amide extension, whereupon the extension is cleaved from the parent drug, resulting in the liberation of the parent drug in its free form. Such an intramolecular cyclization may take place as an enzyme-independent processes under physiological conditions, e.g. via diketopiperazine (DKP) formation. In a prodrug which is converted via DKP formation, the moiety which the parent drug is liberated from upon conversion, is referred to as the "DKP moiety". The prodrug of the invention may have a temporary amide linkage between a dipeptide moiety of the DKP moiety, and an aliphatic amine group of the parent drug. The conversion half-life may be influenced by the structural nature of the DKP moiety. E.g., a desirable conversion half-life may be obtained by using the dipeptides of the DKP moieties exemplified in this application. The conversion half-life may be influenced by the structural nature of the aliphatic amino acid of the parent drug to which the DKP moiety is linked. E.g., a desirable conversion half-life may be obtained by using the N-terminal amino acid residue of the parent drug exemplified in this application. The DKP moiety may be a dipeptide-based extension attached to the parent drug. The DKP moiety may comprise further structural elements than a dipeptide, e.g. a substituent covalently linked to the dipeptide. The DKP moiety may be inactive or may be associated with pharmacological activity. The conversion of the prodrug of the invention takes place predominantly in a non-enzymatic manner. In one aspect of the invention the prodrugs of the invention comprises a DKP moiety.

An example of the nomenclature used for the compounds of the invention comprising a DKP moiety and semaglutide as the parent drug is provided in the following: Gly-$N^{\alpha}$-4-[[(4S)-4-carboxy-4-(17-carboxyheptadecanoylamino)butanoyl]amino]butyl-Gly-semaglutide.

In this compound the DKP moiety comprises a first Gly residue and a second Gly residue interconnected via an amide bond. The moiety "4-[[(4S)-4-carboxy-4-(17-carboxyheptadecanoylamino)butanoyl]amino]butyl" is covalently linked to the nitrogen atom of the second Gly residue. The carboxyl group of the second Gly residue is covalently linked to the N-terminal amino group of the amino acid sequence of semaglutide via an amide bond. The full structure of the compound is depicted below:

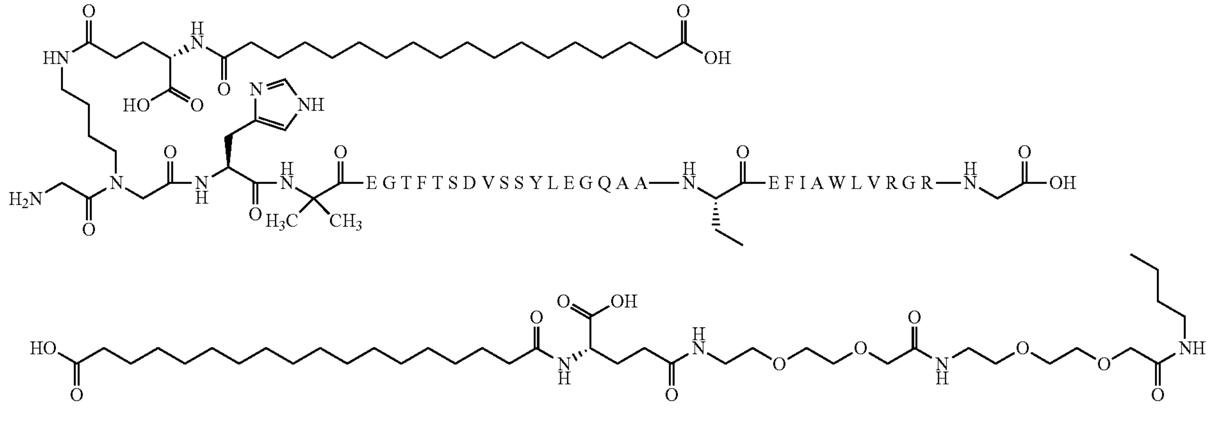

In one embodiment the compound of the invention is a prodrug or a pharmaceutical acceptable salt, ester or amide thereof. In one embodiment the prodrug of the invention is of Formula I: A-Z. In one embodiment of the invention Z is a parent drug. In one embodiment of the invention A is a DKP moiety. In one embodiment of the invention Z comprises a GLP-1 polypeptide. In one embodiment of the invention A is of Formula II:

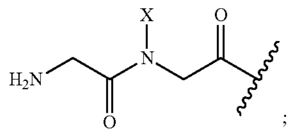

(Formula II)

;

and X is of Formula III:

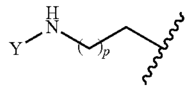

wherein p=1-5 (Formula III);

In one embodiment of the invention Y comprises a lipophilic moiety with a distal carboxylic acid. In one embodiment of the invention the N-terminal amino group of the GLP-1 polypeptide is linked to A via an amide bond. In one embodiment of the invention the N-terminal residue of the GLP-1 polypeptide is His. In one embodiment of the invention the GLP-1 polypeptide is a GLP-1 analogue. In one embodiment of the invention the GLP-1 analogue has maximum of 3 amino acid changes as compared to GLP-1 (7-37) (SEQ ID NO: 1). In one embodiment of the invention the GLP-1 analogue has maximum of 2 amino acid changes as compared to GLP-1 (7-37) (SEQ ID NO: 1). In one embodiment of the invention Z is a GLP-1 derivative. In one embodiment of the invention Z is semaglutide. In one embodiment of the invention X is a substituent. In one embodiment of the invention X has a protracting effect. In one embodiment of the invention Y is a substituent. In one embodiment of the invention Y has a protracting effect.

In one embodiment the compound of the invention is selected from a group consisting of Chem. 14, Chem. 15, Chem. 16, Chem. 17, Chem. 18, Chem. 19, Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, and Chem. 34, or a pharmaceutical acceptable salt, ester or amide thereof. In one embodiment, the compound of the invention is Chem. 14, or a pharmaceutical acceptable salt, ester or amide thereof. In one embodiment, the compound of the invention is Chem. 15, or a pharmaceutical acceptable salt, ester or amide thereof. In one embodiment, the compound of the invention is Chem. 16, or a pharmaceutical acceptable salt, ester or amide thereof. In one embodiment, the compound of the invention is Chem. 17, or a pharmaceutical acceptable salt, ester or amide thereof. In one embodiment, the compound of the invention is Chem. 18, or a pharmaceutical acceptable salt, ester or amide thereof. In one embodiment, the compound of the invention is Chem. 19, or a pharmaceutical acceptable salt, ester or amide thereof. In one embodiment, the compound of the invention is Chem. 20, or a pharmaceutical acceptable salt, ester or amide thereof. In one embodiment, the compound of the invention is Chem. 21, or a pharmaceutical acceptable salt, ester or amide thereof. In one embodiment, the compound of the invention is Chem. 22, or a pharmaceutical acceptable salt, ester or amide thereof. In one embodiment, the compound of the invention is Chem. 23, or a pharmaceutical acceptable salt, ester or amide thereof. In one embodiment, the compound of the invention is Chem. 24, or a pharmaceutical acceptable salt, ester or amide thereof. In one embodiment, the compound of the invention is Chem. 25, or a pharmaceutical acceptable salt, ester or amide thereof. In one embodiment, the compound of the invention is Chem. 26, or a pharmaceutical acceptable salt, ester or amide thereof. In one embodiment, the compound of the invention is Chem. 27, or a pharmaceutical acceptable salt, ester or amide thereof. In one embodiment, the compound of the invention is Chem. 28, or a pharmaceutical acceptable salt, ester or amide thereof. In one embodiment, the compound of the invention is Chem. 29, or a pharmaceutical acceptable salt, ester or amide thereof. In one embodiment, the compound of the invention is Chem. 30, or a pharmaceutical acceptable salt, ester or amide thereof. In one embodiment, the compound of the invention is Chem. 31, or a pharmaceutical acceptable salt, ester or amide thereof. In one embodiment, the compound of the invention is Chem. 32, or a pharmaceutical acceptable salt, ester or amide thereof. In one embodiment, the compound of the invention is Chem. 33, or a pharmaceutical acceptable salt, ester or amide thereof. In one embodiment, the compound of the invention is Chem. 34, or a pharmaceutical acceptable salt, ester or amide thereof.

Semaglutide

Semaglutide is a GLP-1 derivative. Compared to human GLP-1 (7-37), semaglutide has an Aib in position 8 and an Arg in position 34, as well as a substituent covalently attached to the side chain of Lys in position 26. The amino acid sequence of semaglutide is included in the sequence listing as and may be described herein as "[Aib8,Arg34]-GLP-1-(7-37)-peptide". The amino acid sequence of semaglutide is a GLP-1 polypeptide. The amino acid sequence of semaglutide is a GLP-1 analogue which has two amino acid changes as compared to human GLP-1 (7-37). The amino acid sequence of semaglutide is included in the sequence listing as: SEQ ID NO: 2.

The chemical name of the semaglutide is N-$\varepsilon^{26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37)

Semaglutide has the following structure:

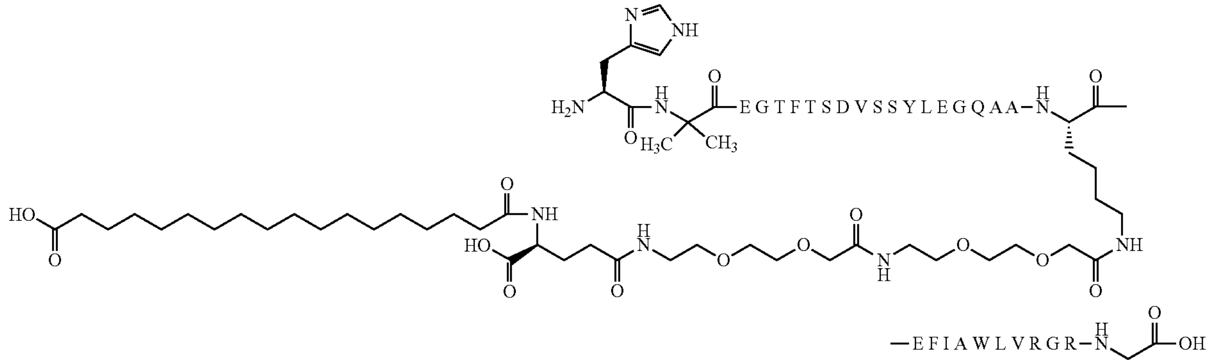

The development of semaglutide is described in Lau et al: "Discovery of the Once-Weekly Glucagon-Like Peptide-1 (GLP-1) Analogue Semaglutide", Journal of Medicinal Chemistry, vol. 58, no. 18 (2015), p. 7370-7380. Semaglutide is marketed as Ozempic® and Rybelsus® for treatment of type 2 diabetes as well as Wegovy® for treatment for chronic weight management. Semaglutide may be prepared using methods known to those skilled in the art, such as those described in WO2006/097537.

Semaglutide has a terminal half-life of about one week in human. Semaglutide is the active drug of Ozempic® which is an injectable prescription medicine for adults with type 2 diabetes that along with diet and exercise may improve blood sugar. The dosing frequency of Ozempic® is once weekly. Semaglutide is also the active drug of Rybelsus® which is an oral prescription medicine for adults with type 2 diabetes that along with diet and exercise may improve blood sugar. Rybelsus® is dosed in a tablet orally once a day. A treatment regime with once weekly oral dosing instead of once daily oral dosing may lead to improved patient convenience and patient compliance. The properties of semaglutide are not optimal for once weekly oral dosing. Semaglutide may be rendered compatible with once weekly oral dosing if it is administered as a suitable prodrug which is converted into semaglutide with a suitable rate once it is absorbed in the body. Designing such a semaglutide prodrug would constitute a significant improvement to the available treatment options. In one embodiment the parent drug of the prodrug of the invention is semaglutide.

Functional Properties

Therapeutic use of pharmacologically active compounds may be hampered by unsuitable pharmacokinetic properties, e.g. because the pharmacokinetic properties are not suitable to reach a desired exposure following administration of the compound. Prodrug technology may be used to improve the pharmacokinetic properties, e.g. to make it suitable for once weekly oral dosing. The exposure level of a parent drug following administration of a prodrug relies on the prodrug to drug conversion half-life, and thus obtaining a suitable conversion half-life may render a compound suitable for a specific dosing regimen (e.g. once weekly administration). The exposure level of a parent drug following administration of a prodrug relies on the observed terminal half-life of the parent drug, and thus obtaining a suitable terminal half-life may render a compound suitable for a specific dosing regimen (e.g. for once weekly administration). The suitability of prodrugs to be administered orally relies on their ability to reach systemic circulation following absorption in the gastrointestinal tract, and thus obtaining a suitable oral bioavailability may render a compound suitable for oral administration (e.g. for once weekly oral administration).

According to a first functional aspect the compounds of the invention has a desirable conversion half-life, e.g. suitable for once weekly administration in human. According to a second functional aspect the compounds of the invention are associated with a desirable observed terminal half-life of the parent drug, e.g. suitable for once weekly administration in human. According to a third functional aspect the compounds of the invention has a desirable oral bioavailability, e.g. suitable for oral administration in human.

Conversion Half-Life

The rate with which the conversion of the prodrug to the drug takes place may be quantified by the conversion half-life. The term "conversion half-life" as used herein refers to the length of time required for the concentration of the prodrug to be reduced to half by conversion. A desirable conversion half-life for a prodrug intended for once weekly oral dosing in human may be 3.0-21 days when measured at pH 7.4 and 37° C.

The prodrug may achieve the desired conversion upon intramolecular cyclization of a terminal dipeptide-based amide extension, whereupon the extension is cleaved from the parent drug, resulting in the liberation of the parent drug in its free form. Such an intramolecular cyclization may take place as an enzyme-independent processes under physiological conditions, e.g. via diketopiperazine (DKP) formation. In a prodrug which is converted via DKP formation, the moiety which the parent drug is liberated from upon conversion, is referred to as the DKP moiety. The conversion half-life relies, inter alia, on the nature of the DKP moiety, and thus the conversion half-life can be improved (e.g. to make it suitable for once weekly oral administration), e.g. by means of molecular design of the DKP moiety, to make the properties of the prodrug suitable for a certain dosing regimen (e.g. for once weekly oral administration).

The conversion half-life may be measured in vitro, e.g. at pH 7.4 and 37° C. The conversion half-life of prodrug to drug may be measured as described in General methods for measuring conversion half-life. In one embodiment the compound of the invention is a prodrug. In one embodiment of the invention the prodrug has a prodrug to parent drug conversion half-life, when measured in vitro at pH 7.4 and 37° C., of at least 3.0 days, preferably at least 3.5 days. In one embodiment of the invention the prodrug has a prodrug to parent drug conversion half-life, when measured in vitro at pH 7.4 and 37° C., of 3.0-21 days, preferably 3.5-21 days, and most preferably 3.5-14 days.

Observed Terminal Half-Life

Many drugs display a biphasic plasma disposition curve, which initially follows a steep slope and subsequently follows a shallow slope. The phase which follows a shallow slope may be referred to as the "terminal phase". The term "terminal half-life" as used herein refers to the time required for the plasma concentration of a compound to be reduced to half during the terminal phase. The terminal half-life of a drug when administered in its free form is different from that of the drug when administered as a prodrug since when administered as a prodrug a continuous liberation of the drug in its free form takes place upon conversion of the prodrug in vivo. Thus, the prodrug acts as a depot from which the drug is slowly released. When administered as a prodrug, the terminal half-life of the parent drug may also be referred to as the "observed terminal half-life". It is to be understood that if the term "observed terminal half-life" when used in context of a prodrug, it refers to the observed terminal half-life of the parent drug that is liberated upon conversion of the prodrug.

An observed terminal half-life suitable for once weekly oral administration in humans, when determined in mini-pigs, may be >80 hours, or preferably be >90 hours, or most preferably >99 hours. An observed terminal half-life suitable for once weekly oral administration in humans, when determined in mini-pigs, may be <250 hours, or may preferably be <180 hours. An observed terminal half-life suitable for once weekly oral administration in humans, when determined in mini-pigs, may be in the range of 90-250 hours, or may preferably be in the range of 99-180 hours.

The observed terminal half-life may be determined in mini-pigs. The observed terminal half-life may be measure as described in

| Compound | Conversion half-life [days] |
|---|---|
| Chem. 14 | 4.4 |
| Chem. 15 | 4.2 |
| Chem. 16 | 4.7 |
| Chem. 17 | 4.4 |
| Chem. 18 | 4.8 |
| Chem. 19 | 3.7 |
| Chem. 20 | 5.6 |
| Chem. 21 | 3.9 |
| Chem. 22 | 7.2 |
| Chem. 23 | 5.5 |
| Chem. 24 | 6.7 |
| Chem. 25 | 6.1 |
| Chem. 26 | 4.9 |
| Chem. 27 | 4.7 |
| Chem. 28 | 6.9 |

-continued

| Compound | Conversion half-life [days] |
|---|---|
| Chem. 29 | 9.1 |
| Chem. 30 | 8.4 |
| Chem. 31 | 8.0 |
| Chem. 32 | 3.6 |
| Chem. 33 | 3.8 |
| Chem. 34 | 3.7 |
| Chem. 35 | 0.7 |
| Chem. 36 | 24.1 |
| Chem. 37 | 2.5 |

General methods for measuring terminal half-life. In one embodiment of the invention the observed terminal half-life of the prodrug of the invention is >80 hours when determined in mini-pigs. In one embodiment of the invention the observed terminal half-life of the prodrug of the invention is >90 hours when determined in mini-pigs. In one embodiment of the invention the observed terminal half-life of the prodrug of the invention is >99 hours when determined in mini-pigs. In one embodiment of the invention the observed terminal half-life of the prodrug of the invention is <180 hours when determined in mini-pigs. In one embodiment of the invention the observed terminal half-life of the prodrug of the invention is 90-150 hours when determined in mini-pigs. In one embodiment of the invention the observed terminal half-life of the prodrug of the invention is 99-120 hours when determined in mini-pigs.

Oral Bioavailability

Oral treatment with pharmacological active compounds may be hampered by poor bioavailability. The term "bioavailability" refers to the capability of a compound to reach systemic circulation following administration, and it may be quantified as the fractional extent of the compound dosage that reaches systemic circulation upon administration. It is desirable that a drug intended for oral administration has a high oral absorption (i.e. a high absorption form the gastrointestinal tract following oral administration) since it may reduce the dosage required to reach the intended systemic concentration of the drug, and thus e.g. reduce tablet size and manufacturing costs.

The term "oral bioavailability" as used herein refers to the capability of a compound to reach systemic circulation following oral administration. The oral bioavailability reflects the extent to which a compound is absorbed in the gastrointestinal tract following oral administration. In other words a high oral bioavailability is associated with a high oral absorption. A high oral bioavailability of a drug is associated with a high drug exposure following oral administration. The oral bioavailability may be measured in a co-formulation with the absorption enhancer sodium N-(8-[2-hydroxybenzoyl]amino) caprylate (SNAC) in beagle dogs as described in WO2019/149880.

The oral bioavailability may be measured as described under General methods for measuring oral bioavailability. In one embodiment, the compound of the invention has a high oral bioavailability. In one embodiment, the compound of the invention has an oral bioavailability that is similar to that of semaglutide. In one embodiment, the compound of the invention has an oral bioavailability that is not inferior to that of semaglutide. In one embodiment, the compound of the invention has an oral bioavailability that is as least as high as that of semaglutide. In one embodiment, the compound of the invention has an oral bioavailability which is suitable for once weekly oral dosing in humans. In one embodiment, the compound of the invention has an oral bioavailability which is determined in Beagle dogs and measured as Cmax/Dose [kg/L]. In one embodiment, the compound of the invention has an oral bioavailability which is measured as Cmax/Dose [kg/L] in Beagle dogs; wherein the Cmax/Dose [kg/L] is >0.10, preferably is >0.15, and most preferably is >0.20. In one embodiment, the compound of the invention has an oral bioavailability which is determined in Beagle dogs and measured as AUC/Dose [kg*hr/L]. In one embodiment, the compound of the invention has an oral bioavailability which is determined in Beagle dogs and measured as AUC/Dose [kg*hr/L]; wherein the AUC/Dose [kg*hr/L] is >2.0, preferably is >5.0, and most preferably is >10.0.

GLP-1 Activity

The term "GLP-1 activity" as used herein refers to the capability of a compound to activate a GLP-1 receptor. Thus, the GLP-1 activity may also be referred to as "GLP-1 potency". The GLP-1 activity may be measured as the in vitro potency. i.e. the performance in a functional GLP-1 receptor assay, more in particular to the ability to stimulate CAMP formation in a cell line expressing the cloned human GLP-1 receptor. The GLP-1 activity may be expressed as an $EC_{50}$ value. The capability of a compound to bind the GLP-1 receptor may also be used as a measure of the GLP-1 activity. In this case the GLP-1 activity may be referred to as the "GLP-1 receptor affinity", and the activity may be expressed as an $IC_{50}$ value. Methods for investigating GLP-1 activity is well-known in the art, and is e.g. described in WO2011/073328, WO2011/080102 and WO2012/062803.

Pharmaceutical Indication/Medical Uses

The present invention also relates to the compound of the invention for use as a medicament. The term "treatment", as used herein, refers to the medical treatment of any human subject in need thereof. The treatment may be preventive, prophylactic, palliative, symptomatic and/or curative. The timing and purpose of said treatment may vary from one individual to another, according to the status of the subject's health.

In one embodiment the compound of the invention may be used for the treatment and/or prevention of (i) all forms of diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

In one embodiment the invention relates to a method of treating one or more of (i), (ii), (iii), (iv), (v), (vi), (vii), (viii), and (ix) comprising administering to a patient in need thereof an effective amount of the compound of the invention, optionally in combination with one or more additional therapeutically active compounds.

In one embodiment the compound of the invention is used for treatment and/or prevention of all forms of diabetes, e.g. hyperglycemia, type 2 diabetes, impaired glucose tolerance, type 1 diabetes, non-insulin dependent diabetes, MODY (maturity onset diabetes of the young), and gestational diabetes, or for diseases where reduction of HbA1C is the treatment goal. In one embodiment the compound may be used for the treatment of cardiovascular diseases, e.g. syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis obliterans), diastolic dysfunction, and/or systolic dysfunction; and/or reduction of blood pressure, such as reduction of systolic blood pressure. In one embodiment the compound is used for the treatment of dyslipidemia and/or diseases where one or more of the following clinical outcomes are the treatment goal: lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein A (apo(A)). In one embodiment the compound may be used for the treatment of non-alcoholic fatty liver disease (NAFLD) and non-alcoholic steatohepatitis (NASH). In one embodiment the compound of the invention is used for treatment and/or prevention of all forms of HF, e.g. heart failure with reduced ejection fraction (HFrEF), heart failure with mid-range ejection fraction (HFmrEF), and/or heart failure with preserved ejection fraction (HFpEF)

In one embodiment, the compound of the invention is used for the treatment of obesity and/or eating disorders where one or more of the following clinical outcomes are the treatment goal: decreasing food intake, increasing energy expenditure, reducing body weight, suppressing appetite, inducing satiety. In one embodiment the compound is used for treatment of neurodegenerative disorders.

The treatment with the compound of the invention may also be combined with one or more additional pharmacologically active substances, e.g. selected from cardiovascular agents, antidiabetic agents, and/or anti-obesity agents. Examples of these pharmacologically active substances are: inotropes, beta adrenergic receptor blockers, HMG-CoA reductase inhibitors, angiotensin II receptor antagonists, angiotensin converting enzyme inhibitors, calcium channel blockers, endothelin antagonists, renin inhibitors, diuretics, aldosterone receptor blockers, endothelin receptor blockers, aldosterone synthase inhibitors, CETP inhibitor, relaxin, PCSK9 inhibitors, BNP and NEP inhibitors, GLP-1 analogues, insulin, sulphonylureas, biguanides, meglitinides, glucosidase inhibitors, glucagon antagonists, DPP-IV inhibitors, SGLT2 inhibitors. The treatment with a compound of this invention may also be combined with heart surgery.

Pharmaceutical Compositions

The present invention also relates to pharmaceutical compositions (also referred to as pharmaceutical formulations) comprising the compound of the invention. In one embodiment the pharmaceutical composition comprising the compound comprises at least one pharmaceutically acceptable excipient.

Pharmaceutical compositions comprising a compound or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance. The excipient may serve various purposes, e.g. as a carrier, vehicle, diluent, tablet aid, and/or to improve administration, and/or absorption of the active substance. The formulation of pharmaceutically active ingredients with various excipients is known in the art, see e.g. Remington: The Science and Practice of Pharmacy (e.g. 19th edition (1995), and any later editions). Additional, optional, ingredients of a pharmaceutical composition include, e.g., wetting agents, emulsifiers, antioxidants, bulking agents, metal ions, oily vehicles, proteins. Non-limiting examples of excipients are: Solvents, diluents, buffers, preservatives, tonicity regulating agents, chelating agents, surfactants, and stabilisers.

The pharmaceutical composition comprising the compound may be of several dosage forms, e.g. a solution, a suspension, a tablet, and a capsule. The pharmaceutical composition comprising the compound may be administered to a patient in need thereof at several sites, e.g. at topical sites such as skin or mucosal sites; at sites which bypass absorption such as in an artery, in a vein, or in the heart; and at sites which involve absorption, such as in the skin, under the skin, in a muscle, orally, or in the abdomen. An administered dose may contain from 0.1 ug/kg to 100 mg/kg of the compound of the invention.

In a preferred embodiment the pharmaceutical composition comprising the compound of the invention are used for the same pharmaceutical indication as indicated for the compound.

Manufacturing Process

The compound of the invention (or fragments thereof), may be prepared by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000. Also or alternatively, the compounds (or fragments hereof) may be produced, in whole or in part, by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines. Those derivatives of the invention which include non-coded amino acids may e.g. be produced as described in the experimental part. Or see e.g., Hodgson et al: "The synthesis of peptides and proteins containing non-natural amino acids", Chemical Society Reviews, vol. 33, no. 7 (2004), p. 422-430.

Specific examples of methods of preparing derivatives of the invention are included in the experimental part.

LIST OF EMBODIMENTS

1. A compound comprising Formula I:

A-Z (Formula I)

wherein Z comprises a GLP-1 polypeptide;

wherein A is of Formula II:

(Formula II)

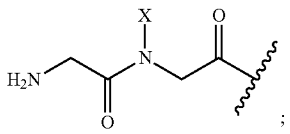
;

wherein X is of Formula III:

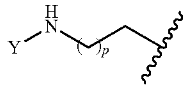

wherein p=1 or 3 (Formula III);

wherein Y comprises a lipophilic moiety with a distal carboxylic acid;

or a pharmaceutical acceptable salt, ester or amide thereof.

2. The compound according to any preceding embodiment, wherein the N-terminal amino group of the GLP-1 polypeptide is linked to A via an amide bond.

3. The compound according to any preceding embodiment, wherein the N-terminal residue of the GLP-1 polypeptide is His.

4. The compound according to any preceding embodiment, wherein Z comprises a GLP-1 analogue.

5. The compound according to any preceding embodiment, wherein Z comprises a GLP-1 analogue which has maximum of 3 amino acid changes as compared to GLP-1 (7-37) (SEQ ID NO: 1).

6. The compound according to any preceding embodiment, wherein Z comprises a GLP-1 analogue which has maximum of 2 amino acid changes as compared to GLP-1 (7-37) (SEQ ID NO: 1).

7. The compound according to any preceding embodiment, wherein Z is a GLP-1 derivative.

8. The compound according to any preceding embodiment, wherein Z is semaglutide.

9. The compound according to any preceding embodiment, wherein Y comprises a moiety selected from a group consisting of Chem. 12 and Chem. 13.

10. The compound according to any preceding embodiment, wherein the lipophilic moiety with a distal carboxylic acid is a moiety selected from a group consisting of Chem. 12 and Chem. 13.

11. The compound according to any preceding embodiment, wherein X is a substituent.

12. The compound according to any preceding embodiment, wherein Y is a substituent.

13. The compound according to any preceding embodiment, wherein Y has a protracting effect.

14. The compound according to any preceding embodiment, wherein Y is a protracting moiety.

15. The compound according to any preceding embodiment, wherein Y comprises a moiety selected from a group consisting of Chem. 12 and Chem. 13.

16. The compound according to any preceding embodiment, wherein Y comprises a moiety selected from a group consisting of Chem. 6 and Chem. 7.

17. The compound according to any preceding embodiment, wherein Y is of Formula IV:

$A_5$-$A_4$-$A_3$-$A_2$-$A_1$- (Formula IV);

wherein $A_1$, $A_2$ and $A_3$ are each individually selected from a group consisting of Chem. 6, Chem. 7, Chem. 8, Chem. 9, Chem. 10, and Chem. 11, or is absent;

wherein $A_4$ is selected from a group consisting of Chem. 6 and Chem. 7;

wherein $A_5$ is selected from the group consisting of Chem. 12 and Chem. 13.

18. The compound according to any preceding embodiment, wherein the residues $A_5$, $A_4$, $A_3$, $A_2$, $A_1$ are interconnected via amide bonds.

19. The compound according to any preceding embodiment, wherein the compound is selected from a group consisting of Chem. 14, Chem. 15, Chem. 16, Chem. 17, Chem. 18, Chem. 19, Chem. 20, Chem. 21, Chem. 22, Chem. 23, Chem. 24, Chem. 25, Chem. 26, and Chem. 27.

20. A compound selected from a group consisting of Chem. 14, Chem. 15, Chem. 16, Chem. 17, Chem. 18, Chem. 19, Chem. 20, Chem. 21, Chem. 22, Chem. 23, Chem. 24, Chem. 25, Chem. 26, and Chem. 27, or a pharmaceutical acceptable salt, ester or amide thereof.

21. A compound, wherein the compound is Chem. 14; or a pharmaceutical acceptable salt, ester or amide thereof.

22. A compound, wherein the compound is Chem. 15; or a pharmaceutical acceptable salt, ester or amide thereof.

23. A compound, wherein the compound is Chem. 16; or a pharmaceutical acceptable salt, ester or amide thereof.

24. A compound, wherein the compound is Chem. 17; or a pharmaceutical acceptable salt, ester or amide thereof.

25. A compound, wherein the compound is Chem. 18; or a pharmaceutical acceptable salt, ester or amide thereof.

26. A compound, wherein the compound is Chem. 19; or a pharmaceutical acceptable salt, ester or amide thereof.

27. A compound, wherein the compound is Chem. 20; or a pharmaceutical acceptable salt, ester or amide thereof.

28. A compound, wherein the compound is Chem. 21; or a pharmaceutical acceptable salt, ester or amide thereof.

29. A compound, wherein the compound is Chem. 22; or a pharmaceutical acceptable salt, ester or amide thereof.

30. A compound, wherein the compound is Chem. 23; or a pharmaceutical acceptable salt, ester or amide thereof.

31. A compound, wherein the compound is Chem. 24; or a pharmaceutical acceptable salt, ester or amide thereof.

32. A compound, wherein the compound is Chem. 25; or a pharmaceutical acceptable salt, ester or amide thereof.

33. A compound, wherein the compound is Chem. 26; or a pharmaceutical acceptable salt, ester or amide thereof.

34. A compound, wherein the compound is Chem. 27; or a pharmaceutical acceptable salt, ester or amide thereof.

35. The compound according to any preceding embodiment, wherein the compound is a prodrug, wherein Z is the parent drug, and wherein the prodrug has a conversion half-life.

36. The compound according to any preceding embodiment, wherein the conversion half-life is measured at 37° C. and pH 7.2.

37. The compound according to any preceding embodiment, wherein the conversion half-life is measured at 37° C. and pH 7.4.

38. The compound according to any preceding embodiment, wherein the conversion half-life is measured at 37° C. and pH 7.2-7.4.

39. The compound according to any preceding embodiment, wherein the conversion half-life is measured in vitro at 37° C. and pH 7.2-7.4.

40. The compound according to any preceding embodiment, wherein the conversion half-life is measured as described in General methods for measuring conversion half-life.

41. The compound according to any preceding embodiment, wherein the conversion half-life is suitable for once weekly oral administration.

42. The compound according to any preceding embodiment, wherein conversion half-life is 5-21 days.

43. The compound according to any preceding embodiment, wherein conversion half-life is 7-21 days.

44. The compound according to any preceding embodiment, wherein conversion half-life is 8-21 days.

45. The compound according to any preceding embodiment, wherein conversion half-life is 9-21 days.

46. The compound according to any preceding embodiment, wherein the conversion half-life is measured at 37° C. and pH 7.2, wherein the conversion half is 5-21 days.

47. The compound according to any preceding embodiment, wherein the conversion half-life is measured at 37° C. and pH 7.2, wherein the conversion half is 7-21 days.

48. The compound according to any preceding embodiment, wherein the conversion half-life is measured at 37° C. and pH 7.2, wherein the conversion half is 8-21 days.

49. The compound according to any preceding embodiment, wherein the conversion half-life is measured at 37° C. and pH 7.2, wherein the conversion half is 9-21 days.

50. The compound according to any preceding embodiment, wherein the conversion half-life is measured at 37° C. and pH 7.4, wherein the conversion half is 5-21 days.

51. The compound according to any preceding embodiment, wherein the conversion half-life is measured at 37° C. and pH 7.4, wherein the conversion half is 7-21 days.

52. The compound according to any preceding embodiment, wherein the conversion half-life is measured at 37° C. and pH 7.4, wherein the conversion half is 8-21 days.

53. The compound according to any preceding embodiment, wherein the conversion half-life is measured at 37° C. and pH 7.4, wherein the conversion half is 9-21 days.

54. The compound according to any preceding embodiment, wherein conversion half-life is a prodrug to drug conversion half-life.

55. The compound according to any preceding embodiment, wherein the compound has an observed terminal half-life.

56. The compound according to any preceding embodiment, wherein the observed terminal half-life is suitable for once weekly oral dosing.

57. The compound according to any preceding embodiment, wherein the observed terminal half-life is >100 hours when determined in mini-pigs.

58. The compound according to any preceding embodiment, wherein the observed terminal half-life is >140 hours when determined in mini-pigs.

59. The compound according to any preceding embodiment, wherein the observed terminal half-life is <250 hours when determined in mini-pigs.

60. The compound according to any preceding embodiment, wherein the observed terminal half-life is <180 hours when determined in mini-pigs.

61. The compound according to any preceding embodiment, wherein the observed terminal half-life is 100-250 hours when determined in mini-pigs.

62. The compound according to any preceding embodiment, wherein the observed terminal half-life is 140-180 hours when determined in mini-pigs.

63. The compound according to any preceding embodiment, wherein the compound has an oral bioavailability.

64. The compound according to any preceding embodiment, wherein the compound has a high oral bioavailability.

65. The compound according to any preceding embodiment, wherein the compound has an oral bioavailability that is similar to that of semaglutide.

66. The compound according to any preceding embodiment, wherein the compound has an oral bioavailability that is not inferior to that of semaglutide.

67. The compound according to any preceding embodiment, wherein the compound has an oral bioavailability that is as least as high as that of semaglutide.

68. The compound according to any preceding embodiment, wherein the oral bioavailability is suitable for once weekly oral dosing.

69. The compound according to any preceding embodiment, wherein the compound is a prodrug.

70. The compound according to any preceding embodiment, wherein semaglutide is N-$\varepsilon^{26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37)

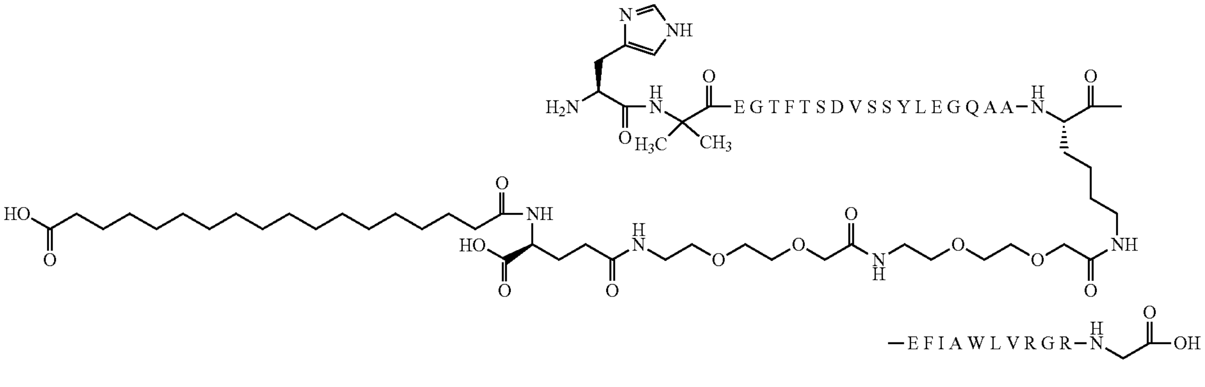

71. A pharmaceutical composition comprising a compound according to any preceding embodiment and at least one pharmaceutical acceptable excipient.

72. The compound according to any preceding embodiment, for use as a medicament.

73. The compound according to any preceding embodiment, for use in the treatment of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

74. The pharmaceutical composition according to any preceding embodiment, for use as a medicament.

75. The pharmaceutical composition according to any preceding embodiment for use in the treatment of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

76. A method for treating (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF) by administering a pharmaceutically relevant amount of a compound according to any preceding embodiment, to a subject in need thereof.

77. A pharmaceutical composition comprising a compound according to any preceding embodiment and at least one pharmaceutical acceptable excipient.

78. A pharmaceutical composition comprising a compound according to any preceding embodiment and at least one pharmaceutical acceptable excipient for the treatment of a disease selected from a group consisting of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

79. Use of compound according to any preceding embodiment, in the manufacture of a medicament for treating a disease selected from a group consisting of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

LIST OF FURTHER EMBODIMENTS

1. A compound comprising Formula I:

A-Z (Formula I)

wherein Z comprises a GLP-1 polypeptide;

wherein A is of Formula II:

(Formula II)

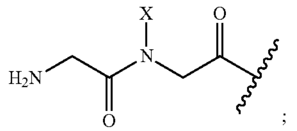

;

wherein X is of Formula III:

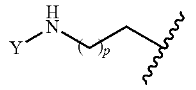

wherein p=1-5 (Formula III);

wherein Y comprises a lipophilic moiety with a distal carboxylic acid;

or a pharmaceutical acceptable salt, ester or amide thereof.

2. The compound according to any preceding embodiment, wherein the N-terminal amino group of the GLP-1 polypeptide is linked to A via an amide bond.

3. The compound according to any preceding embodiment, wherein the N-terminal residue of the GLP-1 polypeptide is His.

4. The compound according to any preceding embodiment, wherein the GLP-1 polypeptide is a GLP-1 analogue.

5. The compound according to any preceding embodiment, wherein the GLP-1 polypeptide is a GLP-1 analogue; and wherein the GLP-1 analogue has maximum of 3 amino acid changes as compared to GLP-1 (7-37) (SEQ ID NO: 1).

6. The compound according to any preceding embodiment, wherein the GLP-1 polypeptide is a GLP-1 analogue; and wherein the GLP-1 analogue has maximum of 2 amino acid changes as compared to GLP-1 (7-37) (SEQ ID NO: 1).

7. The compound according to any preceding embodiment, wherein Z is a GLP-1 derivative.

8. The compound according to any preceding embodiment, wherein Z is semaglutide.

9. The compound according to any preceding embodiment, wherein Y comprises a moiety selected from a group consisting of Chem. 12 and Chem. 13.

10. The compound according to any preceding embodiment, wherein the lipophilic moiety with a distal carboxylic acid is a moiety selected from a group consisting of Chem. 12 and Chem. 13.

11. The compound according to any preceding embodiment, wherein X is a substituent.

12. The compound according to any preceding embodiment, wherein X has a protracting effect.

13. The compound according to any preceding embodiment, wherein Y is a substituent.

14. The compound according to any preceding embodiment, wherein Y is a protracting moiety.

15. The compound according to any preceding embodiment, wherein Y comprises a moiety selected from a group consisting of Chem. 12 and Chem. 13.

16. The compound according to any preceding embodiment, wherein Y comprises a moiety selected from a group consisting of Chem. 6 and Chem. 7.

17. The compound according to any preceding embodiment, wherein Y is of Formula IV:

$$A_5\text{-}A_4\text{-}A_3\text{-}A_2\text{-}A_1\text{-} \quad \text{(Formula IV);}$$

wherein $A_1$, $A_2$ and $A_3$ are each individually selected from a group consisting of Chem. 6, Chem. 7, Chem. 8, Chem. 9, Chem. 10, and Chem. 11, or is absent;

wherein $A_4$ is selected from a group consisting of Chem. 6 and Chem. 7;

wherein $A_5$ is selected from the group consisting of Chem. 12 and Chem. 13.

18. The compound according to any preceding embodiment, wherein the residues $A_5$, $A_4$, $A_3$, $A_2$, $A_1$ are interconnected via amide bonds.

19. The compound according to any preceding embodiment, wherein the compound is selected from a group consisting of Chem. 14, Chem. 15, Chem. 16, Chem. 17, Chem. 18, Chem. 19, Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, and Chem. 34.

20. A compound selected from a group consisting of Chem. 14, Chem. 15, Chem. 16, Chem. 17, Chem. 18, Chem. 19, Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, and Chem. 34, or a pharmaceutical acceptable salt, ester or amide thereof.

21. A compound, wherein the compound is Chem. 14; or a pharmaceutical acceptable salt, ester or amide thereof.

22. A compound, wherein the compound is Chem. 15; or a pharmaceutical acceptable salt, ester or amide thereof.

23. A compound, wherein the compound is Chem. 16; or a pharmaceutical acceptable salt, ester or amide thereof.

24. A compound, wherein the compound is Chem. 17; or a pharmaceutical acceptable salt, ester or amide thereof.

25. A compound, wherein the compound is Chem. 18; or a pharmaceutical acceptable salt, ester or amide thereof.

26. A compound, wherein the compound is Chem. 19; or a pharmaceutical acceptable salt, ester or amide thereof.

27. A compound, wherein the compound is Chem. 20; or a pharmaceutical acceptable salt, ester or amide thereof.

28. A compound, wherein the compound is Chem. 21; or a pharmaceutical acceptable salt, ester or amide thereof.

29. A compound, wherein the compound is Chem. 22; or a pharmaceutical acceptable salt, ester or amide thereof.

30. A compound, wherein the compound is Chem. 23; or a pharmaceutical acceptable salt, ester or amide thereof.

31. A compound, wherein the compound is Chem. 24; or a pharmaceutical acceptable salt, ester or amide thereof.

32. A compound, wherein the compound is Chem. 25; or a pharmaceutical acceptable salt, ester or amide thereof.

33. A compound, wherein the compound is Chem. 26; or a pharmaceutical acceptable salt, ester or amide thereof.

34. A compound, wherein the compound is Chem. 27; or a pharmaceutical acceptable salt, ester or amide thereof.

35. A compound, wherein the compound is Chem. 28; or a pharmaceutical acceptable salt, ester or amide thereof.

36. A compound, wherein the compound is Chem. 29; or a pharmaceutical acceptable salt, ester or amide thereof.

37. A compound, wherein the compound is Chem. 30;
    or a pharmaceutical acceptable salt, ester or amide thereof.
38. A compound, wherein the compound is Chem. 31;
    or a pharmaceutical acceptable salt, ester or amide thereof.
39. A compound, wherein the compound is Chem. 32;
    or a pharmaceutical acceptable salt, ester or amide thereof.
40. A compound, wherein the compound is Chem. 33;
    or a pharmaceutical acceptable salt, ester or amide thereof.
41. A compound, wherein the compound is Chem. 34;
    or a pharmaceutical acceptable salt, ester or amide thereof.

42. The compound according to any preceding embodiment, wherein the compound is a prodrug and Z is a parent drug.

43. The compound according to any preceding embodiment, wherein the compound is a prodrug and A is a DKP moiety.

44. The compound according to any preceding embodiment, wherein the compound is a prodrug, Z is a parent drug, and A is a DKP moiety.

45. The compound according to any preceding embodiment, wherein the compound is a prodrug and A dipeptide with a substituent.

46. The compound according to any preceding embodiment, wherein the compound has a conversion half-life.

47. The compound according to any preceding embodiment, wherein the compound has a conversion half-life suitable for once-weekly dosing.

48. The compound according to any preceding embodiment, wherein the compound has a long conversion half-life.

49. The compound according to any preceding embodiment, wherein the conversion half-life is measured in vitro at 37° C. and pH 7.4.

50. The compound according to any preceding embodiment, wherein the conversion half-life is measured as described in General methods for measuring conversion half-life.

51. The compound according to any preceding embodiment, wherein the conversion half-life is at least 3.0 days.

52. The compound according to any preceding embodiment, wherein the conversion half-life is at least 3.5 days.

53. The compound according to any preceding embodiment, wherein the conversion half-life is at least 4 days.

54. The compound according to any preceding embodiment, wherein the conversion half-life is 3.0-21.0 days.

55. The compound according to any preceding embodiment, wherein the conversion half-life is 3.0-14.0 days.

56. The compound according to any preceding embodiment, wherein the conversion half-life is 3.5-14.0 days.

57. The compound according to any preceding embodiment, wherein the conversion half-life is measured at 37° C. and pH 7.4, wherein the conversion half is 3.5-14 days.

58. The compound according to any preceding embodiment, wherein the conversion half-life is measured at 37° C. and pH 7.4, wherein the conversion half is 4-14 days.

59. The compound according to any preceding embodiment, wherein conversion half-life is a prodrug to drug conversion half-life.

60. The compound according to any preceding embodiment, wherein the parent drug has an observed terminal half-life upon administration of the prodrug.

61. The compound according to any preceding embodiment, wherein the parent drug has an observed terminal half-life suitable for once-weekly dosing upon administration of the prodrug.

62. The compound according to any preceding embodiment, wherein the parent drug has a long observed terminal half-life upon administration of the prodrug.

63. The compound according to any preceding embodiment, wherein the observed terminal half-life is suitable for once weekly oral dosing in human upon administration of the prodrug.

64. The compound according to any preceding embodiment, wherein the observed terminal half-life of the parent drug, determined upon administration of the prodrug in mini-pigs, is >80 hours.

65. The compound according to any preceding embodiment, wherein the observed terminal half-life of the parent drug, determined upon administration of the prodrug in mini-pigs, is >90 hours.

66. The compound according to any preceding embodiment, wherein the observed terminal half-life of the parent drug, determined upon administration of the prodrug in mini-pigs, is >99 hours.

67. The compound according to any preceding embodiment, wherein the observed terminal half-life of the parent drug, determined upon administration of the prodrug in mini-pigs, is <180 hours.

68. The compound according to any preceding embodiment, wherein the observed terminal half-life of the parent drug, determined upon administration of the prodrug in mini-pigs, is 80-150 hours.

69. The compound according to any preceding embodiment, wherein the observed terminal half-life of the parent drug, determined upon administration of the prodrug in mini-pigs, is 90-150 hours.

70. The compound according to any preceding embodiment, wherein the observed terminal half-life of the parent drug, determined upon administration of the prodrug in mini-pigs, is 99-120 hours.

71. The compound according to any preceding embodiment, wherein the compound has an oral bioavailability.

72. The compound according to any preceding embodiment, wherein the compound has a high oral bioavailability.

73. The compound according to any preceding embodiment, wherein the compound has an oral bioavailability that is similar to that of semaglutide.

74. The compound according to any preceding embodiment, wherein the compound has an oral bioavailability that is not inferior to that of semaglutide.

75. The compound according to any preceding embodiment, wherein the compound has an oral bioavailability that is as least as high as that of semaglutide.

76. The compound according to any preceding embodiment, wherein the oral bioavailability is suitable for once weekly oral dosing in humans.

77. The compound according to any preceding embodiment, wherein the oral bioavailability is determined in Beagle dogs.

78. The compound according to any preceding embodiment, wherein the oral bioavailability is determined in Beagle dogs upon administration of tablets containing 3 mg of the compound, 300 mg sodium N-(8-(2-hydroxybenzoyl) amino)caprylate (SNAC) and 7.7 mg magnesium stearate.

79. The compound according to any preceding embodiment, wherein the oral bioavailability is measured as Cmax/Dose [kg/L].

80. The compound according to any preceding embodiment, wherein the oral bioavailability is measured as AUC/Dose [kg*hr/L].

81. The compound according to any preceding embodiment, wherein the oral bioavailability is determined as described in General methods for measuring oral bioavailability.

82. The compound according to any preceding embodiment, wherein the oral bioavailability is measured as Cmax/Dose [kg/L] in Beagle dogs; and wherein the Cmax/Dose [kg/L] is >0.10.

83. The compound according to any preceding embodiment, wherein the oral bioavailability is measured as Cmax/Dose [kg/L] in Beagle dogs; and wherein the Cmax/Dose [kg/L] is >0.15.

84. The compound according to any preceding embodiment, wherein the oral bioavailability is measured as Cmax/Dose [kg/L] in Beagle dogs; and wherein the Cmax/Dose [kg/L] is >0.20.

85. The compound according to any preceding embodiment, wherein the oral bioavailability is measured as AUC/Dose [kg*hr/L] in Beagle dogs; and wherein the AUC/Dose [kg*hr/L] is >2.0.

86. The compound according to any preceding embodiment, wherein the oral bioavailability is measured as AUC/Dose [kg*hr/L] in Beagle dogs; and wherein the AUC/Dose [kg*hr/L] is >5.0.

87. The compound according to any preceding embodiment, wherein the oral bioavailability is measured as AUC/Dose [kg*hr/L] in Beagle dogs; and wherein the AUC/Dose [kg*hr/L] is >10.0.

88. The compound according to any preceding embodiment, wherein semaglutide is N-$\varepsilon^{26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37)

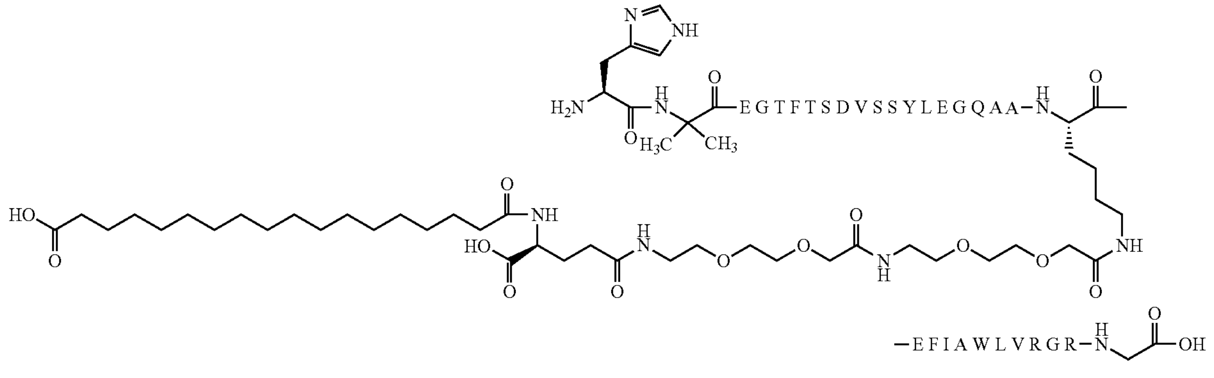

89. A pharmaceutical composition comprising a compound according to any preceding embodiment and at least one pharmaceutical acceptable excipient.

90. A pharmaceutical composition comprising a compound selected from a group consisting of Chem. 14, Chem. 15, Chem. 16, Chem. 17, Chem. 18, Chem. 19, Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, and Chem. 34, or a pharmaceutical acceptable salt, ester or amide thereof; and at least one pharmaceutical acceptable excipient 91. The compound according to any preceding embodiment, for use as a medicament.

92. The compound according to any preceding embodiment, for use in the treatment of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

93. The pharmaceutical composition according to any preceding embodiment, for use as a medicament.

94. The pharmaceutical composition according to any preceding embodiment for use in the treatment of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

95. A method for treating (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF) by administering a pharmaceutically relevant amount of a compound according to any preceding embodiment, to a subject in need thereof.

96. A pharmaceutical composition comprising a compound according to any preceding embodiment and at least one pharmaceutical acceptable excipient.

97. A pharmaceutical composition comprising a compound according to any preceding embodiment and at least one pharmaceutical acceptable excipient for the treatment of a disease selected from a group consisting of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

98. Use of compound according to any preceding embodiment, in the manufacture of a medicament for treating a disease selected from a group consisting of (i) diabetes, (ii) obesity, (iii) non-alcoholic fatty liver disease (NAFLD) and non-alcoholic steatohepatitis (NASH), (iv) cardiovascular disease, (v) neurodegenerative disorders, (vi) chronic kidney disease (CKD), (vii) diabetic kidney disease (DKD), (viii) peripheral arterial disease (PAD), and/or (ix) heart failure (HF).

EXAMPLES

This experimental part starts with a list of abbreviations and is followed by a section on the general methods for compound preparation and a section on the methods for measuring properties relevant for the exposure profile. A number of specific examples have been included in each of the sections to illustrate the invention. All example compounds were prepared according to the general methods described herein. The exemplified compounds comprises an amino acid sequence of:

SEQ ID NO: 3

Abbreviations

Aib: α-aminoisobutyric acid
Boc: t-butyloxycarbonyl
CAD: Charged Aerosol Detector
Collidine: 2,4,6-trimethylpyridine
DCM: Dichloromethane
DIC: Diisopropylcarbodiimide
DKP: Diketopiperazine
DMF: Dimethylformamide
D-PBS Dulbecco's phosphate-buffered saline
EDTA: Ethylenediaminetetraacetic acid
Fmoc: 9-fluorenylmethyloxycarbonyl
Abg(N3) N-(4-azidobutyl)-glycine
Ado 8-amino-3,6-dioxaoctanoic acid
Aeg(N3) N-(2-azidoethyl)-glycine
HFIP: 1,1,1,3,3,3-hexafluoro-2-propanol or hexafluoroisopropanol
HPLC: High Performance Liquid Chromatography
LC: Liquid Chromatography
LCMS: Liquid Chromatography Mass Spectroscopy
MeCN Acetonitrile
MQ: Milli-Q
MS: Mass Spectroscopy
Mtt: 4-methyltrityl
OtBu: tert-butoxy
Oxyma Pure®: Cyano-hydroxyimino-acetic acid ethyl ester
Pbf: 2,2,4,6,7-pentamethyldihydrobenzofuran-5-sulfonyl
PBS Phosphate Buffered Saline
RP: Reverse Phase
RP-HPLC: Reverse Phase High Performance Liquid Chromatography
Sar Sarcosine
RT: Room Temperature
SEC: Size-Exclusion Chromatography
SNAC: Sodium N-(8-(2-hydroxybenzoyl)amino)caprylate
SPPS: Solid Phase Peptide Synthesis
tBu: tert-butyl
TCEP: tris(2-carboxyethyl)phosphine
TFA: trifluoroacetic acid
TIPS: triisopropylsilane
Trt: triphenylmethyl (trityl)
UPLC: Ultra Performance Liquid Chromatography
UV: Ultraviolet

General Methods for Preparation of the Compounds of the Invention

In one aspect the derivatives of the invention may be prepared as described in the examples herein. In one aspect the derivatives of the invention may be prepared as known in the art, i.e. the preparation of peptides may be produced by classical peptide synthesis, e.g. solid phase peptide synthesis using Boc or Fmoc chemistry or other well-established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Fatty Acid- and Special Amino Acid Building Blocks

Synthesis of octadecanedioic acid mono-tert-butyl ester was carried out as described in WO2010102886 (pages 27-28). The corresponding mono-tert-butyl esters of C14, C16- and C20 diacid were prepared accordingly. Synthesis of 10-(4-tert-butoxycarbonylphenoxy)decanoic acid and 11-(4-tert-butoxycarbonylphenoxy)undecanoic acid were carried out as described for 9-(4-tert-butoxycarbonylphenoxy) undecanoic acid in WO2011080103 (page 131).

Fmoc-Ado-OH, H-Aeg(Fmoc)-OH*HCl, Fmoc-Aib-OH, Fmoc-Glu-OtBu, Boc-Gly-OH, Fmoc-Sar-OH, Fmoc-Aeg (N3)-OH, Fmoc-Abg(N3)-OH, 3-azidopropan-1-amine, 3-azidopentane-1-amine and 3-azidohexane-1-amine were obtained from Novabiochem, Iris Biotech or Enamine.

Synthesis of the Building Block Boc-Gly-Aeg(Fmoc)-OH

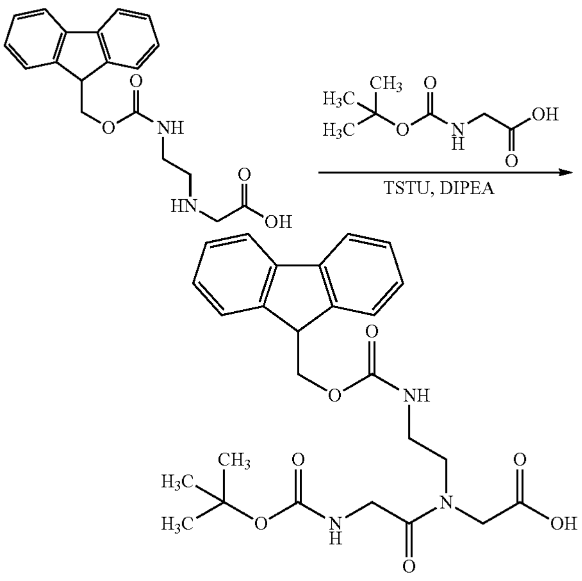

Boc-Gly-OH (11.6 g, 66.0 mmol) was dissolved in DMF (300 mL) followed by addition of N,N,N',N'-tetramethyl-O—(N-succinimidyl) uronium tetrafluoroborate (TSTU, 19.9 g, 66.0 mmol) and N,N-diisopropylethylamine (DIPEA, 35.0 mL, 199 mmol). The mixture was stirred for 30 minutes and H-Aeg(Fmoc)-OH*HCl (25.0 g, 66.0 mmol) was introduced in one portion. Reaction mixture was stirred for 3.5 hours. Solvent was removed under reduced pressure. The residue was diluted with ethyl acetate (600 mL), washed with water (1×500 mL), 10% aqueous solution of citric acid (1×500 mL), 10% aqueous solution of sodium bicarbonate (1×500 mL) and brine (1×500 mL). The organic layer was dried over anhydrous sodium sulfate, filtered and concentrated in vacuo. The residue was purified by flash column chromatography (Silicagel 60, 0.040-0.063 mm; eluent: dichloromethane/methanol 4:1) to give pure Boc-Gly-Aeg (Fmoc)-OH as a yellow foam. Yield: 27.0 g (82%). $^1$H NMR spectrum (300 MHZ, AcOD-$d_4$, $\delta_H$): 7.81 (d, J=7.5 Hz, 2H); 7.65 (d, J=7.4 Hz, 2H); 7.47-7.27 (m, 4H); 4.57 (bs, 2H); 4.32-3.96 (m, 5H); 3.46 (bs, J=42.0 Hz, 4H); 1.46 (s, 9H). LC-MS m/z calc: 498.2 $(M+H)^+$. LC-MS m/z found: 498.2 $(M+H)^+$.

Peptide Synthesis

The preparation of the peptide was carried out with SPPS using Fmoc based chemistry on a Prelude Solid Phase Peptide Synthesizer or a Symphony X from Protein Technologies. The Fmoc-protected amino acids used in the methods were the standard recommended: Fmoc-Ala-OH, Boc-Ala-OH, Fmoc-Arg(Pbf)-OH, Fmoc-Asp(OtBu)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Phe-OH, Fmoc-Pro-OH, Fmoc-Ser(tBu)-OH, Fmoc-Thr (tBu)-OH, Fmoc-Trp(Boc)-OH, Fmoc-Tyr(tBu)-OH, Fmoc-Val-OH and Fmoc-Lys(Mtt)-OH supplied from e.g. Anaspec, Bachem, Iris Biotech or NovabioChem.

A Wang resin preloaded with Fmoc-protected Glycine (Fmoc-Gly-Wang) was used. The subsequent amino acids were introduced in a stepwise procedure by a Prelude or Symphony X peptide synthesizer following the SPPS principles.

Fmoc-deprotection was achieved with 20% piperidine in DMF for 2×10 min. Introduction of the substituent at the alpha-position of the N-terminal amino acid was accomplished using a standard Fmoc-protected amino acid. The peptide couplings were performed with DIC/Oxyma Pure. Amino acid/Oxyma Pure solutions (0.3 M/0.3 M in DMF at a molar excess of 3-4-fold) was added to the resin first. Then, the same molar equivalent of DIC was added (3 M in DMF). Coupling time was 1.5 hours. In some cases, the coupling time was increased or the coupling step was repeated to achieve satisfactory levels of coupling. A subsequent capping step was performed with 1 M acetic anhydride in DMF or DIPEA.

Introduction of a substituent on the primary amino-group of an amino-ethyl-glycine (Aeg) was achieved using Boc-Gly-Aeg(Fmoc)-OH. Alternatively, introduction of a substituent on the primary amino-group of an amino-ethyl-glycine (Aeg) or amino-butyl-glycine (Abg) was achieved using Fmoc-Aeg($N_3$)—OH or Fmoc-Abg($N_3$)—OH respectively, followed by Fmoc-deprotection and coupling with Boc-Gly-OH using standard conditions. The azido-protection group was reduced with TCEP (3 eq.) in DMF (2 hours), followed by MQ Water/DMF (25:75) (1 hour). The resin was washed with DMF (6×). Hereafter, the introduction of a substituent on the primary amino-group was introduced with standard conditions.

Introduction of a amino-propyl-glycine, amino-pentyl-glycine and amino-hexyl-glycine was achieved by bromo-acetylation of the alfa-amine of peptidyl bound semaglutide with bromoacetyl anhydride (10 eq.) in DCM (10 hours). After draining and washing with DMF (6×), the resin was treated with 3-azidopropan-1-amine, 3-azidopentane-1-amine or 3-azidohexane-1-amine respectively (10 eq.) and DIPEA (20 eq.) in DMF (3 hours). The resin was washed with DMF (6×) before coupling with Boc-Gly-OH using standard conditions. The azido-protection group was subsequently reduced with TCEP (3 eq.) in DMF (2 hours), followed by MQ Water/DMF (25:75) (1 hour). Hereafter, introduction of a substituent on the primary amino-group was introduced using standard conditions.

For the introduction of a substituent on the epsilon-nitrogen of a Lysine in position 26, Fmoc-Lys (Mtt)-OH was used. The Mtt group was removed by treatment with HFIP/DCM/TIPS (75:22.5:2.5) (2×20 min), and subsequently washed with DCM and DMF before the substituent was introduced at the epsilon-nitrogen of the Lys.

General Cleavage Method

The peptides were cleaved with TFA/TIPS/H2O/DTT (95:2:2:1) for 2 hours, after which the solution was drained into cold diethyl ether and centrifuged. The ether was decanted off, and the peptide was washed with ether two times.

General Method for Purification and Quantification of the Derivative

The crude peptide was dissolved in 50% Acetic Acid in MQ water and purified by reversed-phase preparative HPLC (Waters Delta Prep 4000) on a column comprising C18-silica gel. Elution was performed with an increasing gradient of MeCN in MQ water containing 0.1% TFA. Relevant fractions were analysed with UPLC. Fractions containing the pure target peptide were pooled. The resulting solution was analysed (UPLC, LCMS) and the peptide derivative was quantified using a CAD specific HPLC detector (Vanquish Thermo-Fischer HPLC-CAD). The product was dispensed into glass vials. The vials were capped with Millipore glass fibre prefilters. Freeze-drying afforded the trifluoroacetate salt of the derivative as a white solid.

General LCMS Method

| | |
|---|---|
| System | LC-system: Waters Acquity UPLC H Class<br>Column: Waters Acquity BEH, C-18, 1.7 μm, 2.1 mm × 50 mm<br>Detector: Waters Xevo G2-XS QTof |
| Detector setup | Ionisation method: ES<br>Scanning range: 50-4000 amu<br>Operating mode: MS resolution mode<br>positive/ne: positive mode<br>Voltage: Capillary 3.00 kV<br>Sample cone: 40 V<br>Source: 80 V<br>Temperature: Source 150° C.<br>Desolvation: 500° C.<br>Scantime: 0.500 s<br>Interscandelay: 0.014 s |
| Conditions | Linear gradient: 5% to 95% B<br>Gradient run-time: 4.0 minutes<br>Total run-time: 7.0 minutes<br>Flow rate: 0.4 mL/min<br>Column temperature: 40° C. |
| Eluents | Solvent A: 99,90% MQ-water, 0.1% formic acid<br>Solvent B: 99.90% acetonitrile, 0.1% formic acid<br>Solvent C: 99.90% MQ water 0.1% TFA<br>Gradient : A 90-0%, B 5-95%, C 5% |

-continued

| | |
|---|---|
| Results | Found mass is the monoisotopic mass found ((M + z)/z) of the compound. Calculated mass is the monoisotopic mass (M + z)/z calculated for the compound. |

Example 1

Gly-$N^{\alpha}$-2-[[(4S)-4-carboxy-4-(15-carboxypentadecanoylamino)butanoyl]amino]ethyl-Gly-semaglutide Chem. 14

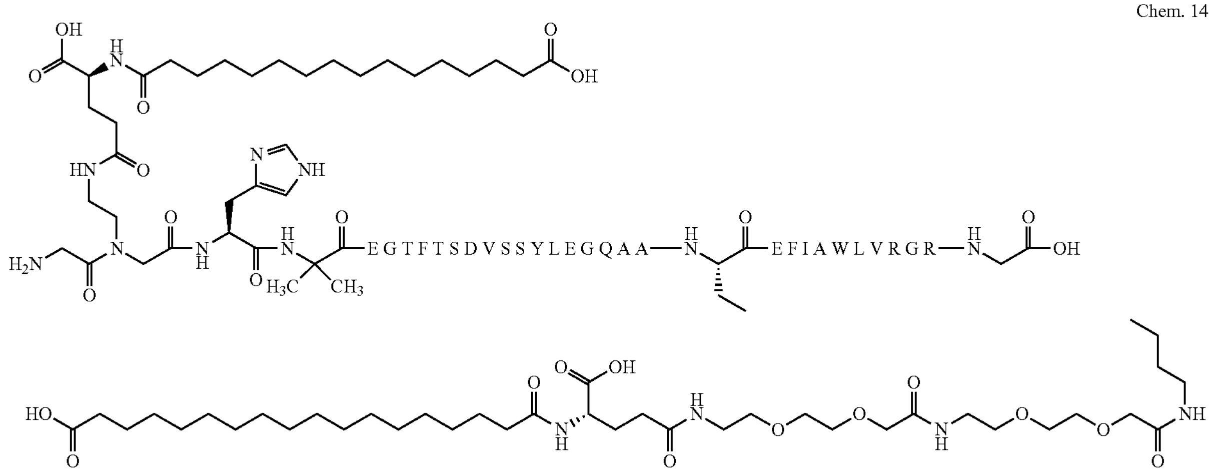

LCMS

Calculated mass: M/3=1556.15; M/4=1167.36; M/5=934.09.

Found mass M/3=1556.06; M/4=1167.30; M/5=934.04.

Example 2

Gly-$N^{\alpha}$-4-[[(4S)-4-carboxy-4-(17-carboxyheptadecanoylamino)butanoyl]amino]butyl-Gly-semaglutide Chem. 15

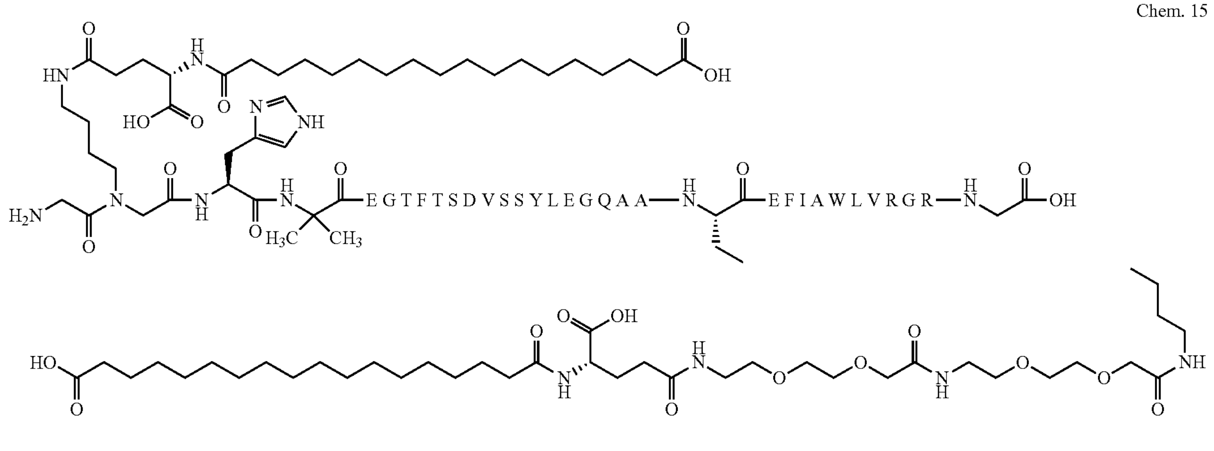

Calculated mass: M/3=1574.84; M/4=1181.38; M/5=945.30.

Found mass: M/3 1575.05; M/4=1181.54; M/5=945.43.

Example 3
Gly-$N^{\alpha}$-2-[[(4S)-4-carboxy-4-(17-carboxyheptadecanoylamino)butanoyl]amino]ethyl-Gly-semaglutide
Chem. 16
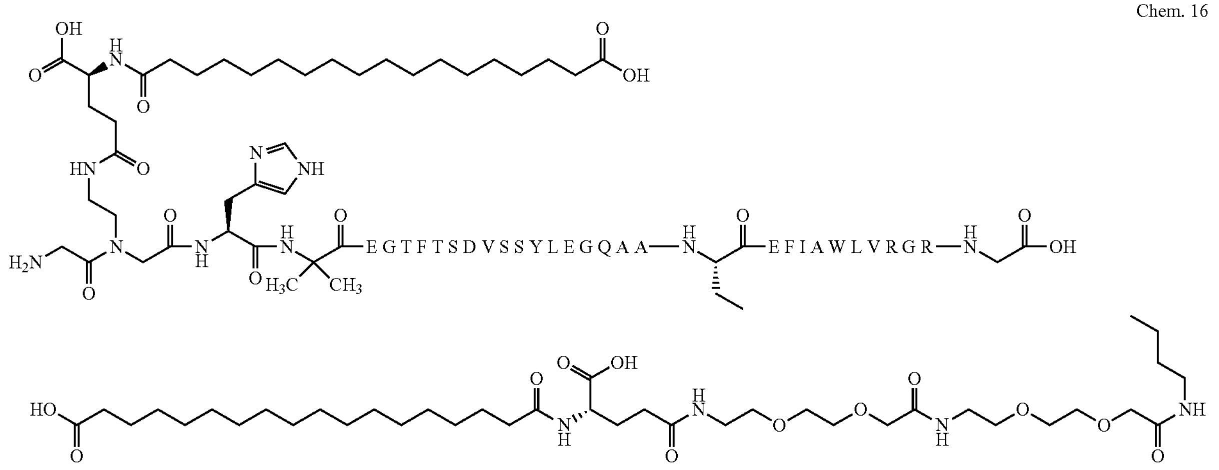
LCMS
Calculated mass: M/3=1565.49; M/4=1174.37; M/5=939.67.
Found mass: M/3=1565.71; M/4=1174.53; M/5=939.83.
Example 4
Gly-$N^{\alpha}$-2-[[(4S)-4-carboxy-4-(13-carboxytridecanoylamino)butanoyl]amino]ethyl-Gly-semaglutide
Chem. 17
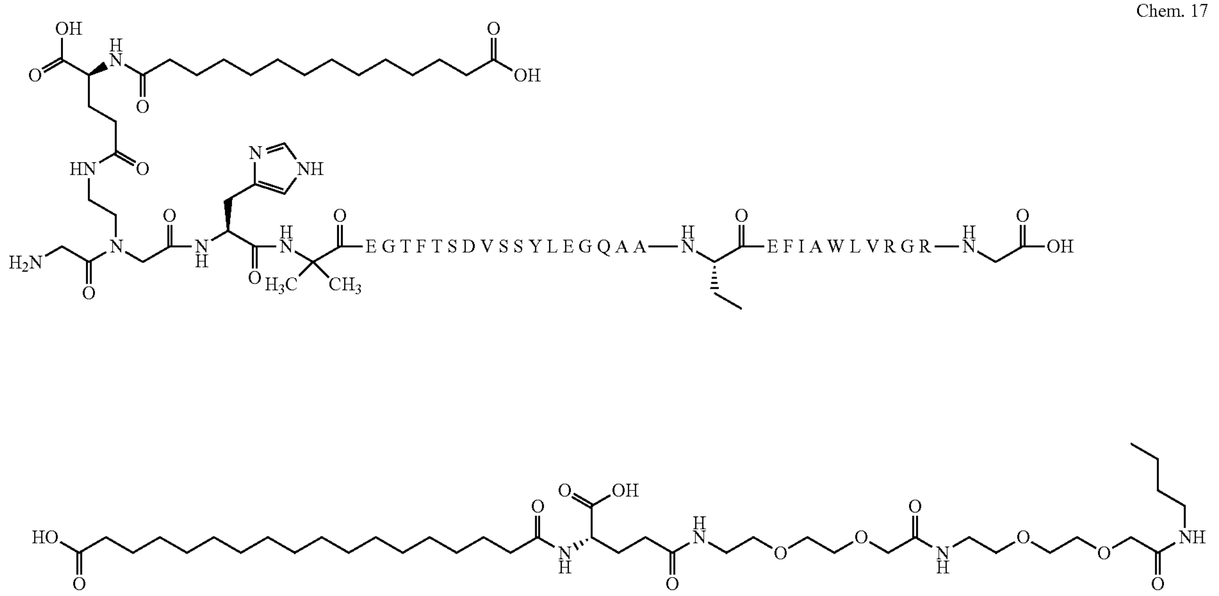
LCMS
Calculated mass: M/3=1546.81; M/4=1160.36; M/5=928.49.
Found mass: M/3=1546.83; M/4=1160.37; M/5=928.49.

Example 5

Gly-$N^{\alpha}$-2-[[(4S)-4-carboxy-4-[10-(4-carboxyphenoxy)decanoylamino]butanoyl]amino]ethyl-Gly-semaglutide Chem. 18

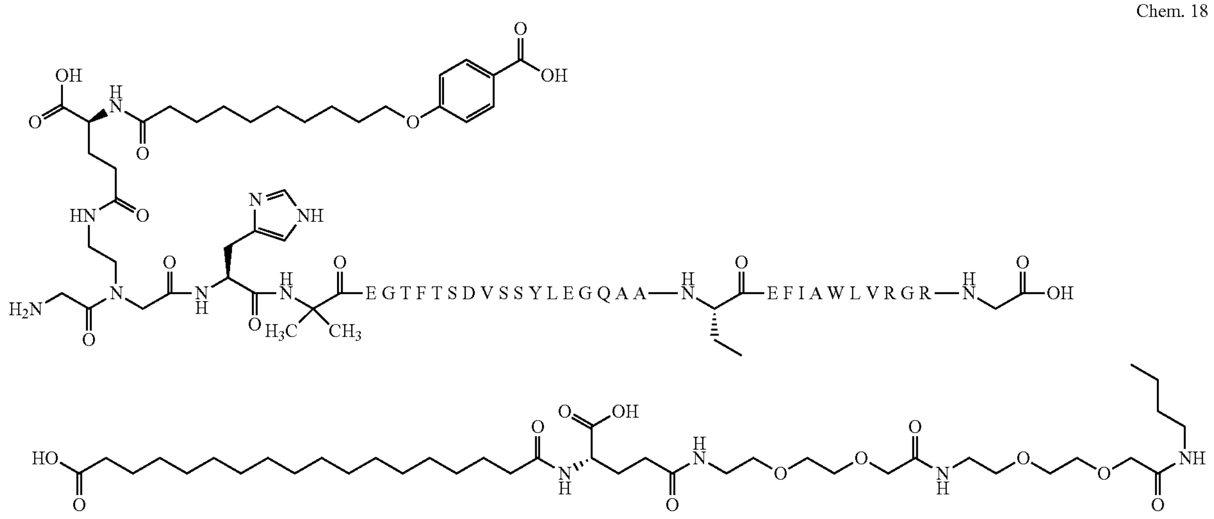

LCMS

Calculated mass: M/3=1563.47; M/4=1172.86; M/5=938.49.

Found mass: M/3=1563.48; M/4=1172.85; M/5=938.48.

Example 6

Gly-$N^{\alpha}$-2-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]ethyl-Gly-semaglutide Chem. 19

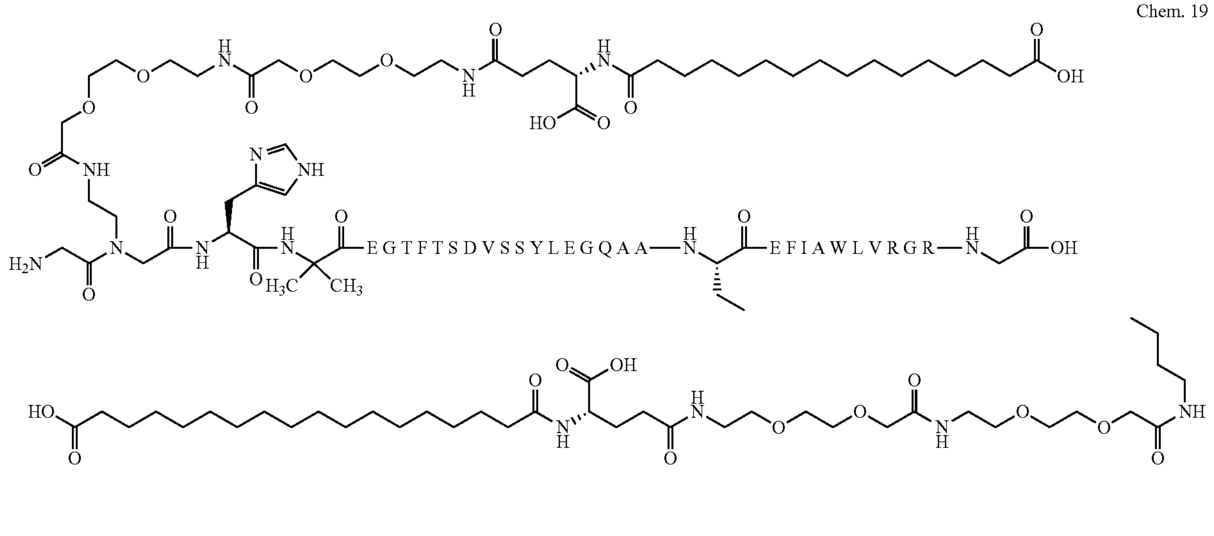

LCMS

Calculated mass: M/3=1652.86; M/4=1239.90; M/5=992.12.

Found mass: M/3=1652.89; M/4=1239.91; M/5=992.13.

Example 7

Gly-N$^{\alpha}$-2-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]ethyl-Gly-semaglutide Chem. 20

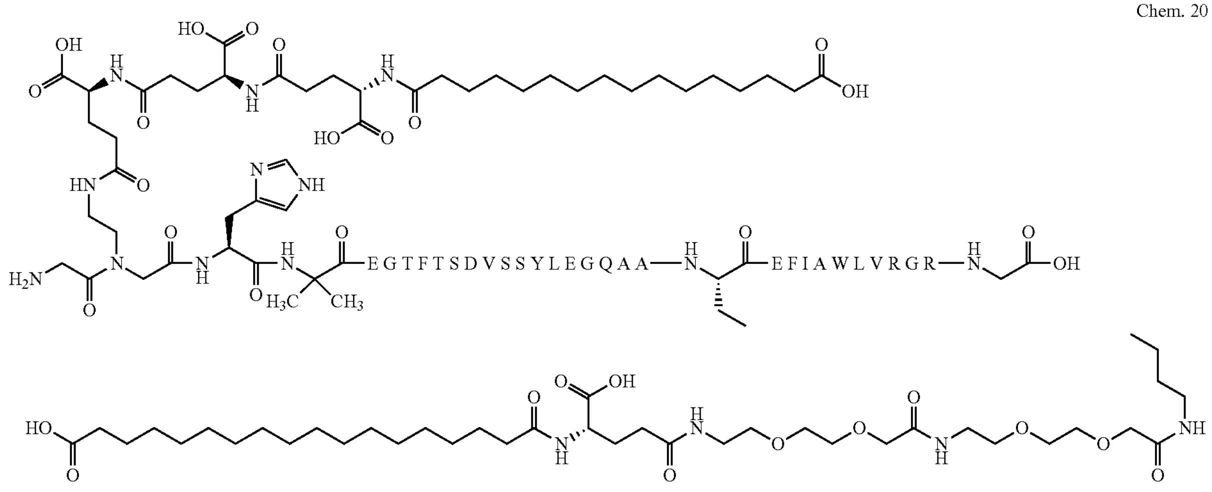

LCMS

Calculated mass: M/3=1642.18; M/4=1231.88; M/5=985.71.

Found mass: M/3=1642.20; M/4=1231.89; M/5=985.72.

Example 8

Gly-N$^{\alpha}$-4-[[(4S)-4-carboxy-4-(15-carboxypentadecanoylamino)butanoyl]amino]butyl-Gly-semaglutide Chem. 21

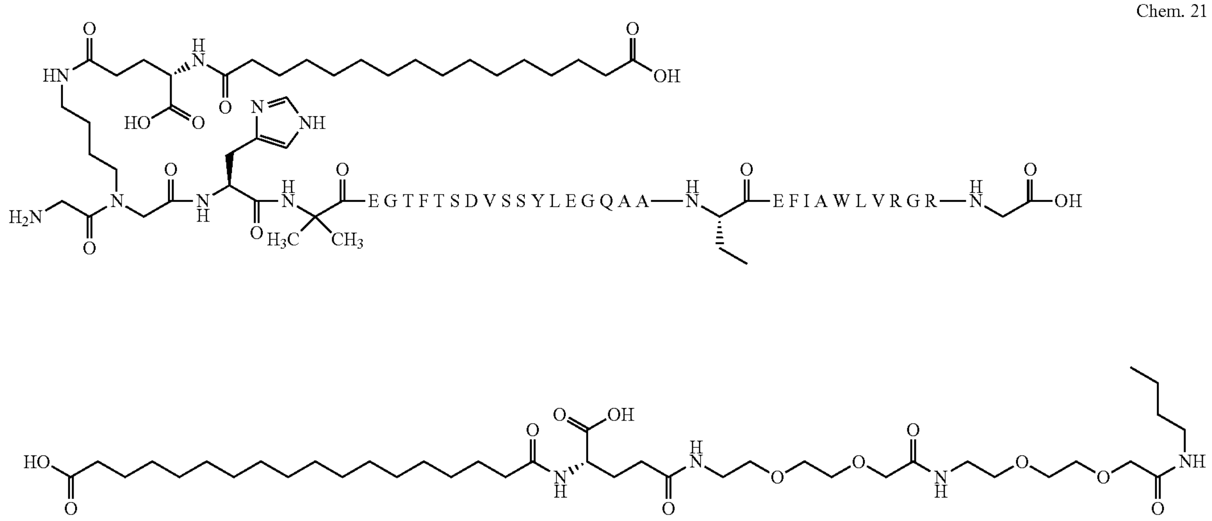

LCMS

Calculated mass: M/3=1565.49; M/4=1174.37; M/5=939.70.

Found mass: M/3=1565.76; M/4=1174.57; M/5=939.87.

Example 9

Gly-N$^{\alpha}$-2-[[(2S)-4-carboxy-2-[[(2S)-4-carboxy-2-[[(4S)-4-carboxy-4-(15-carboxypentadecanoylamino)butanoyl]amino]butanoyl]amino]butanoyl]amino]ethyl-Gly-semaglutide Chem. 22

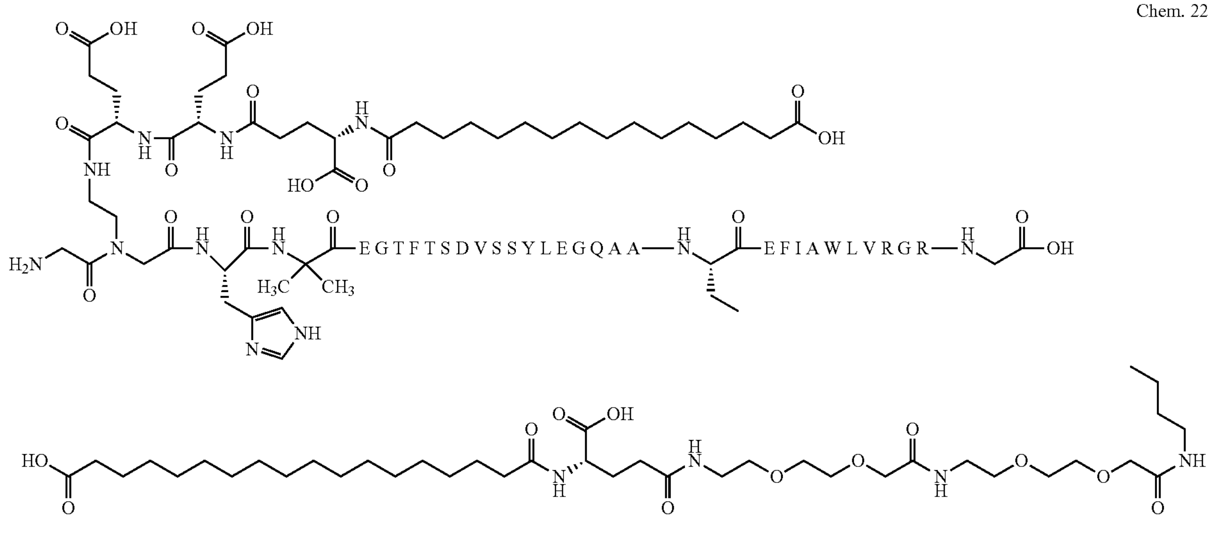

LCMS

Calculated mass: M/3=1642.18; M/4=1231.88; M/5=985.71.

Found mass: M/3=1642.19; M/4=1231.89; M/5=985.71.

Example 10

Gly-N$^{\alpha}$-2-[[(2S)-4-carboxy-2-[[(2S)-4-carboxy-2-[[(4S)-4-carboxy-4-(15-carboxypentadecanoylamino)butanoyl]amino]butanoyl]amino]butanoyl]amino]ethyl-Gly-semaglutide Chem. 23

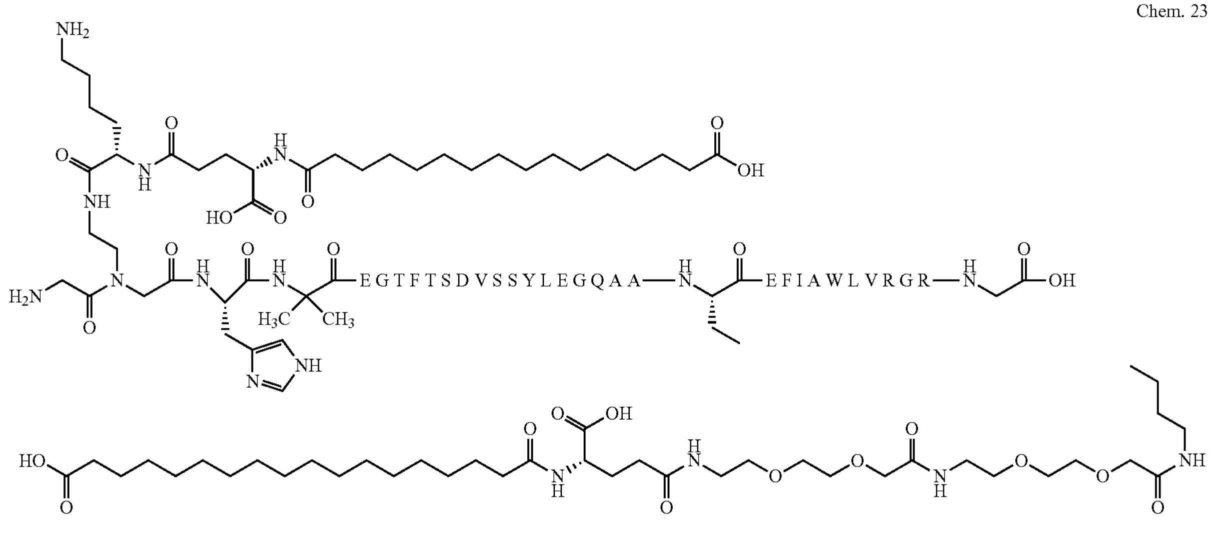

LCMS

Calculated mass: M/3=1598.85; M/4=1199.39; M/5=959.71.

Found mass: M/3=1598.87; M/4=1199.40; M/5=959.72.

Example 11

Gly-N$^{\alpha}$-2-[[(2S)-2-[[(4S)-4-carboxy-4-(15-carboxypentadecanoylamino)butanoyl]amino]-3-hydroxypropanoyl]amino]ethyl-Gly-semaglutide Chem. 24

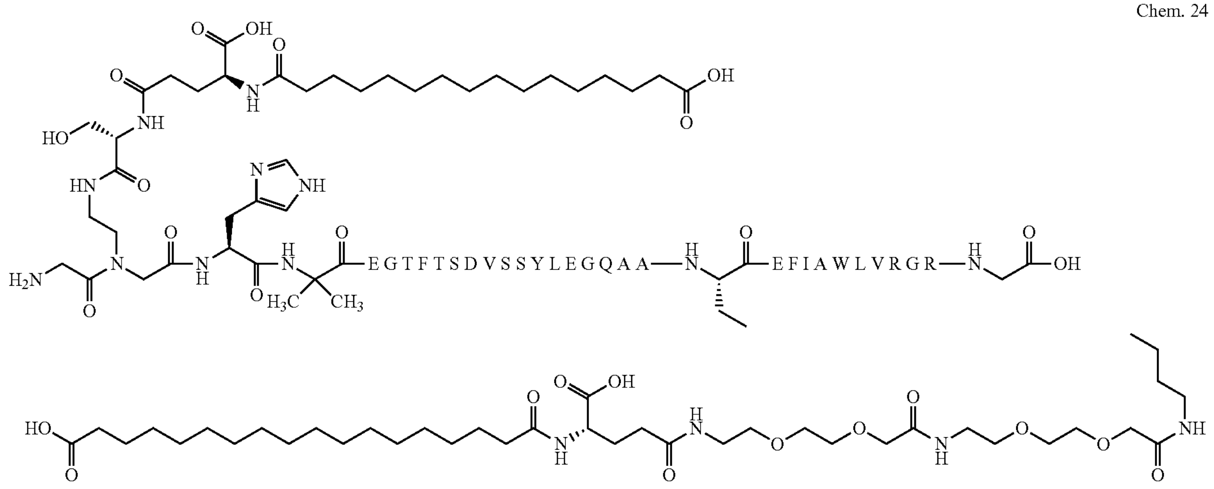

LCMS

Calculated mass: M/3=1585.16; M/4=1189.12; M/5=951.50.

Found mass: M/3=1585.17; M/4=1189.11; M/5=951.49.

Example 12

Gly-N$^{\alpha}$-2-[[2-[[(4S)-4-carboxy-4-(15-carboxypentadecanoylamino)butanoyl]amino]acetyl]amino]ethyl-Gly-semaglutide Chem. 25

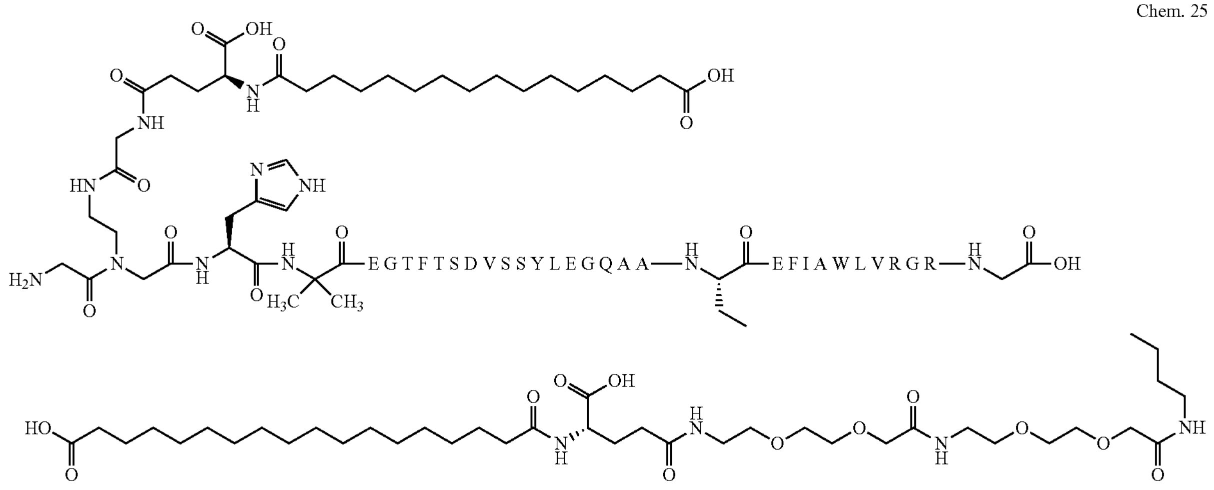

LCMS

Calculated mass: M/3=1575.16; M/4=1181.63; M/5=945.50.

Found mass: M/3=1575.18; M/4=1181.63; M/5=945.50.

Example 13
Gly-$N^{\alpha}$-2-[[(4S)-4-carboxy-4-[11-(4-carboxyphenoxy)undecanoylamino]butanoyl]amino]ethyl-Gly-semaglutide
Chem. 26
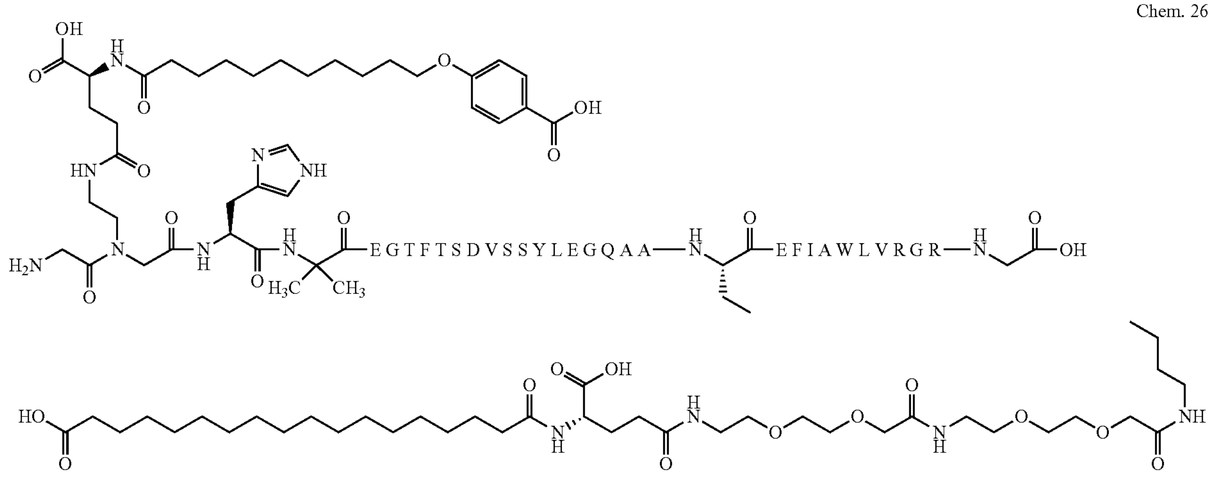
LCMS
Calculated mass: M/3=1568.14; M/4=1176.35; M/5=941.28.
Found mass: M/3=1568.16; M/4=1176.36; M/5=941.29.
Example 14
Gly-$N^{\alpha}$-2-[[(4S)-4-carboxy-4-(19-carboxynonadecanoylamino)butanoyl]amino]ethyl-Gly-semaglutide
Chem. 27
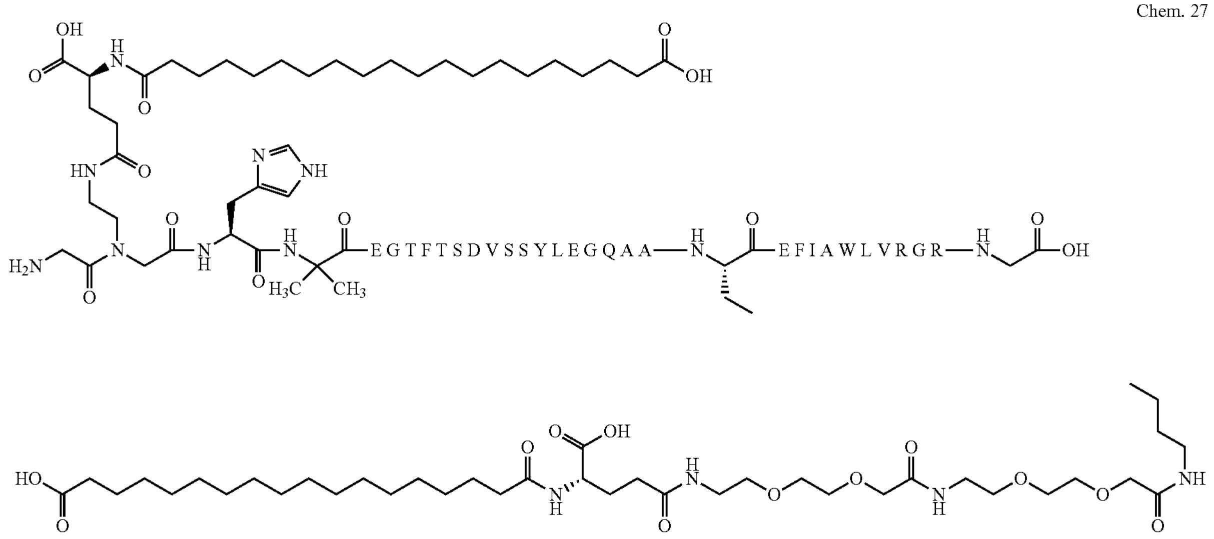
LCMS
Calculated mass: M/3=1574.84; M/4=1181.39; M/5=945.31.
Found mass: M/3=1574.85; M/4=1181.38; M/5=945.30.

Example 15

Gly-N$^{\alpha}$-2-[[(4S)-4-carboxy-4-[[(4S)-4-carboxy-4-(17-carboxyheptadecanoylamino)butanoyl]amino]butanoyl]amino]ethyl-Gly-semaglutide Chem. 28

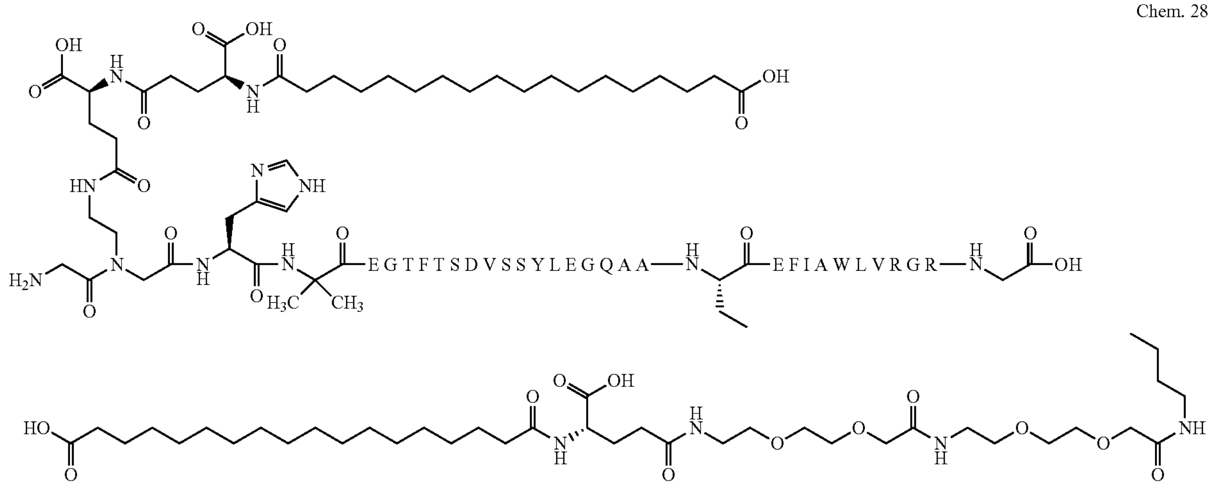

LCMS

Calculated mass: M/3=1608.51; M/4=1206.63; M/5=965.50.

Found mass: M/3=1608.57; M/4=1206.67; M/5=965.53.

Example 16

Gly-N$^{\alpha}$-2-[[(2S)-2-[[(4S)-4-carboxy-4-(17-carboxyheptadecanoylamino)butanoyl]amino]-3-hydroxypropanoyl]amino]ethyl-Gly-semaglutide Chem. 29

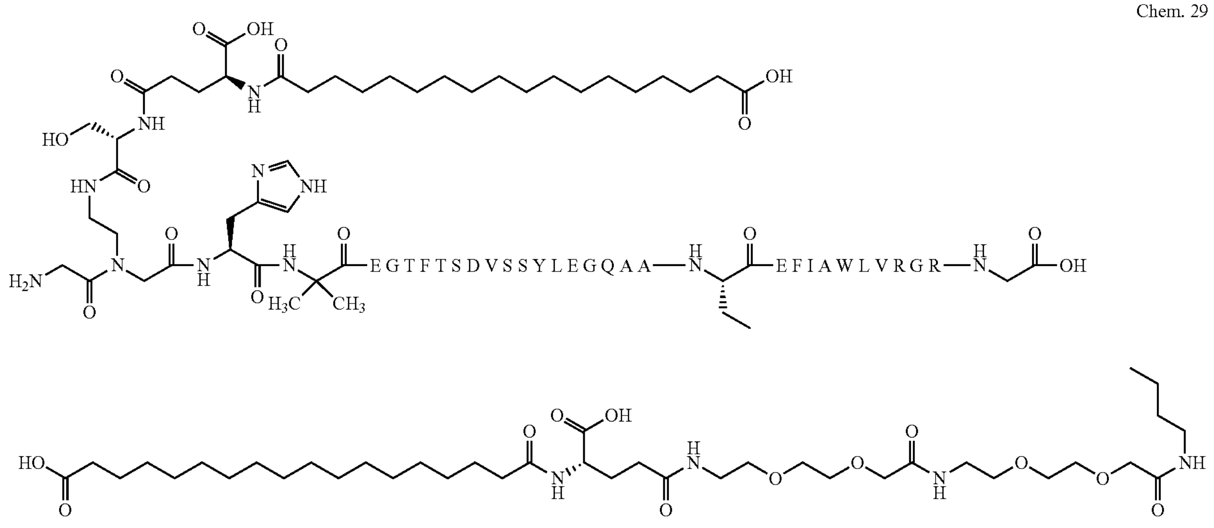

LCMS

Calculated mass: M/3=1595.46; M/4=1196.85.

Found mass: M/3=1595.23; M/4=1196.90.

Example 17
Gly-N$^{\alpha}$-2-[[2-[[(4S)-4-carboxy-4-(17-carboxyheptadecanoylamino)butanoyl]amino]acetyl]amino]ethyl-Gly-semaglutide
Chem. 30
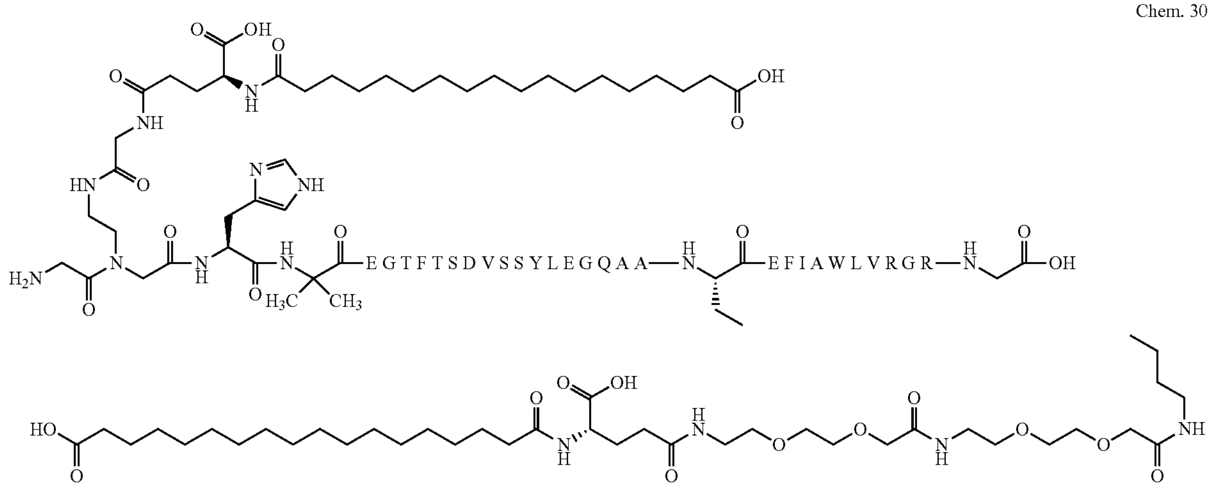
LCMS
Calculated mass: M/3=1584.50; M/4=1188.62; M/5=951.10.
Found mass: M/3=1584.57; M/4=1188.66; M/5=951.12.
Example 18
Gly-N$^{\alpha}$-2-[[(4S)-4-carboxy-2-(17-carboxyheptadecanoylamino)butanoyl]amino]ethyl-Gly-semaglutide
Chem. 31
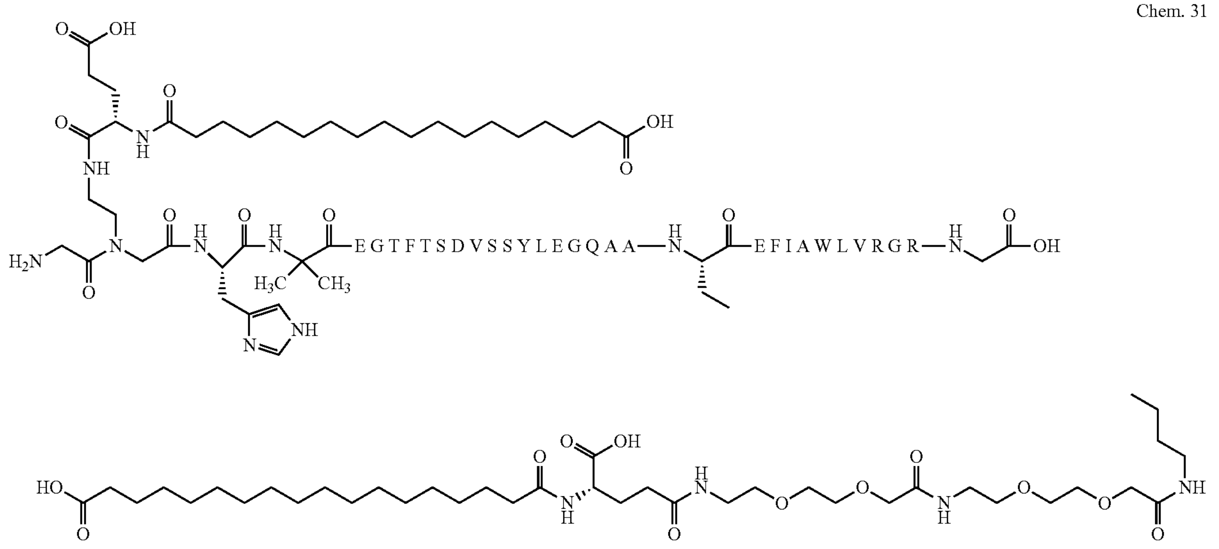
LCMS
Calculated mass: M/3=1566.44; M/4=1175.08.
Found mass: M/3=1566.13; M/4=1174.86.

Example 19
Gly-N$^{\alpha}$-3-[[(4S)-4-carboxy-4-(15-carboxypentadecanoylamino)butanoyl]amino]propyl-Gly-semaglutide
Chem. 32
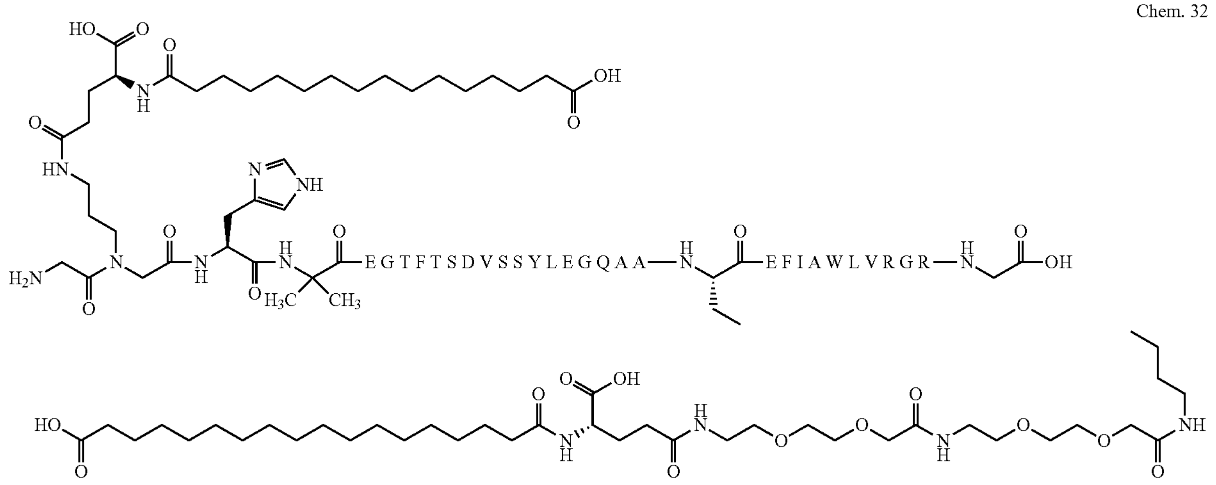
LCMS
Calculated mass: M/3=1560.82; M/4=1170.87; M/5=936.89.
Found mass: M/3=1560.89; M/4=1170.91; M/5=937.12.
Example 20
Gly-N$^{\alpha}$-5-[[(4S)-4-carboxy-4-(15-carboxypentadecanoylamino)butanoyl]amino]pentyl-Gly-semaglutide
Chem. 33
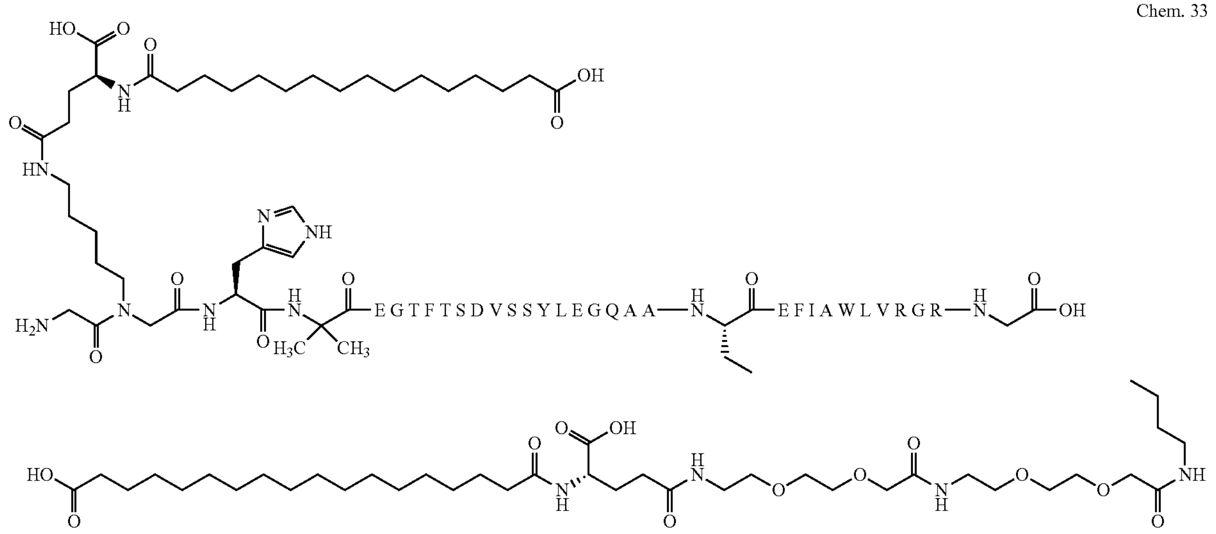
LCMS
Calculated mass: M/3=1570.16; M/4=1177.87; M/5=942.50.
Found mass: M/3=1570.25; M/4=1177.93; M/5=942.53.

Example 21
Gly-N$^{\alpha}$-6-[[(4S)-4-carboxy-4-(15-carboxypentadecanoylamino)butanoyl]amino]hexyl-Gly-semaglutide
Chem. 34
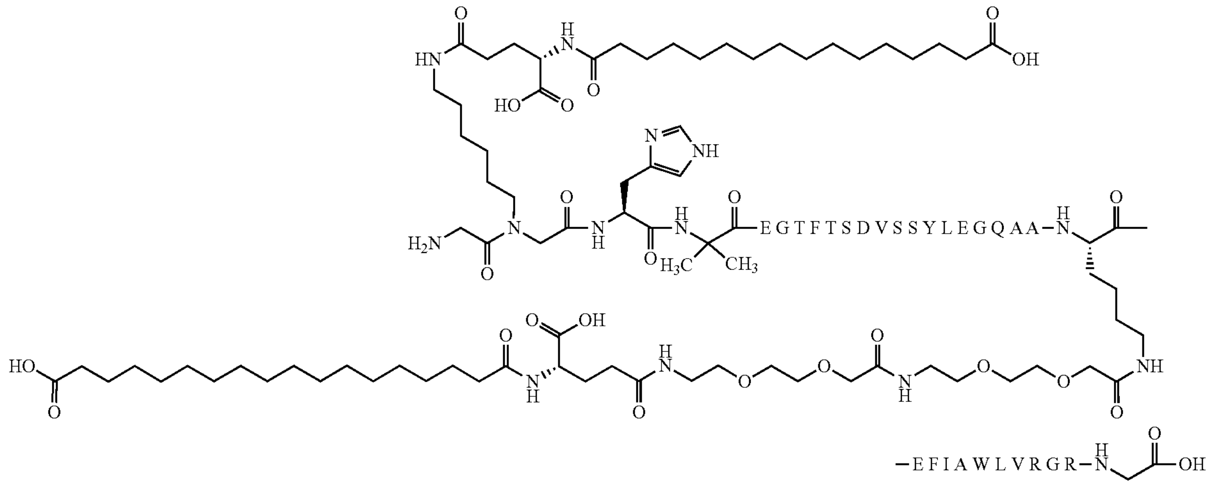
LCMS
Calculated mass: M/3=1574.84; M/4=1181.38; M/5=945.30.
Found mass: M/3=1574.92; M/4=1181.43; M/5=945.34.
Example 22—Reference Compound
Arg-N$^{\alpha}$-4-[[(4S)-4-carboxy-4-(15-carboxypentadecanoylamino)butanoyl]amino]butyl-Gly-semaglutide
Chem. 35
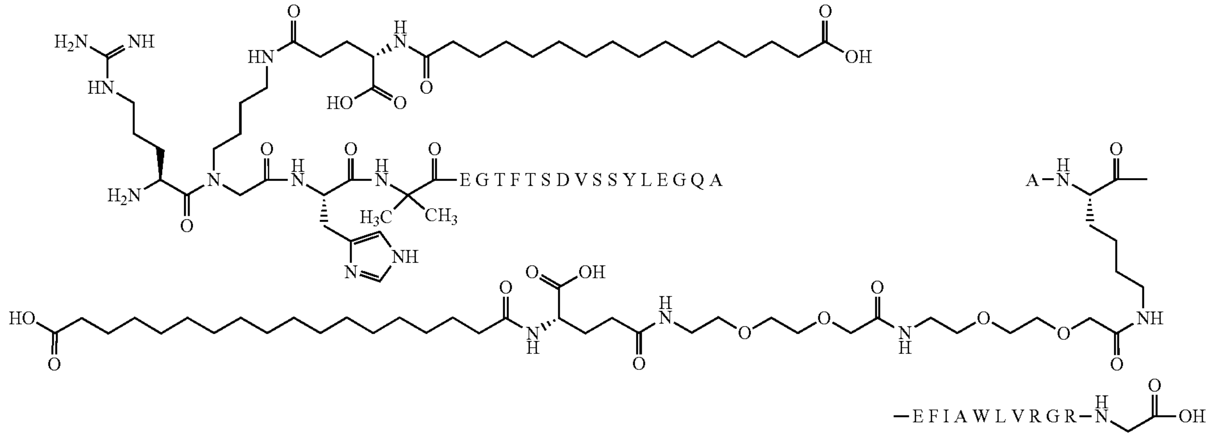
LCMS
Calculated mass: M/3=1598.52; M/4=1199.14; M/5=959.51.
Found mass: M/3=1598.80; M/4=1199.36; M/5=959.69.

Example 23—Reference Compound

Gly-$N^{\alpha}$-2-(aminoethyl)-Gly-semaglutide

Chem. 36

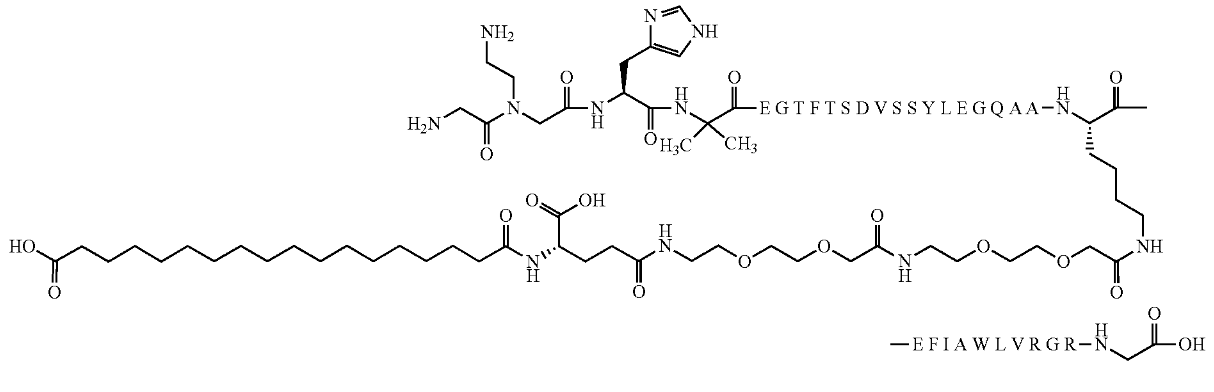

LCMS

Calculated mass: M/3=1423.73; M/4=1068.05; M/5=854.64.

Found mass: M/3=1423.79; M/4=1068.09; M/5=854.67.

Example 24—Reference Compound $N^{\alpha}$-octadecanoyl-DLys-Sar-semaglutide Chem. 37

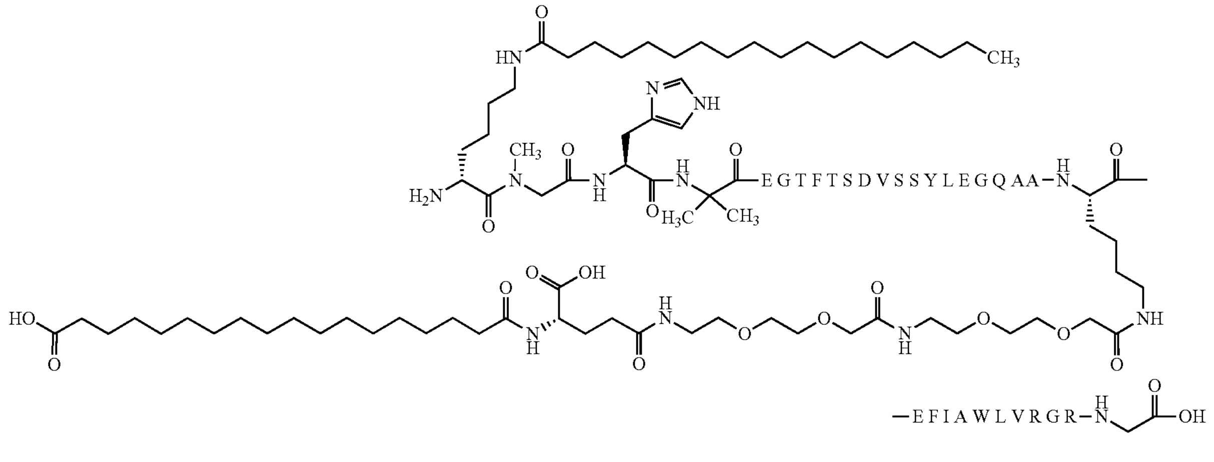

LCMS

Calculated mass: M/3=1526.50; M/4=1145.13; M/5=916.30.

Found mass: M/3=1526.76; M/4=1145.32; M/5=916.46.

General Methods for Measuring Conversion Half-Life

The assay was performed to investigate the conversion half-life of prodrug to drug of the prodrugs of the invention. The conversion half-life was investigated in vitro at pH 7.4 upon incubation at 37° C.

Peptide stock solutions were prepared by dissolving freeze-dried powder in PBS buffer to a target of 200 μM. PBS-buffer was Dulbecco's Phosphate Buffered Saline without $CaCl_2$ and $MgCl_2$, gibco 14190-094 adjusted to pH=7.4. The pH of the peptide stock solutions was adjusted to 7.4 with 0.02 M HCl or 0.02M NaOH. Samples were filled in Agilent HPLC vials with fixed insert. Vials were capped to prevent evaporation. The HPLC vials were incubated at 37° C. and samples were withdrawn at different time points over a period of 2 weeks, flash frozen at −80° C., and stored at −20° C. until analysis.

Sample analysis was carried out using UPLC coupled to UV detection at 215 nm and MS (UPLC-UV-MS). One μl of sample was injected on to a Waters Acquity UPLC with a flow-through-needle injection system and on to a Waters Acquity CSH C18 column (1*150 mm), with a particle size of 1.7 μm and held at 55° C. A flow-rate of 100 μl/min was delivered with a Binary solvent manager pump having 0.1% formic acid in water as solvent A and 0.1% formic acid in acetonitrile as solvent B. Gradient elution was carried out using 15-32% B from 0 to 4 min followed by 32 to 48% B from 4 to 54 min.

The identity of the prodrug was confirmed by MS and the peak purity, area %, from the UV signal at 215 nm was plotted as the natural logarithm against time and the slope (k) was used to calculate the first order half-life (T½) =T½=Ln(2)/k.

Example 25

The prodrug to drug conversion half-life of the compounds of the invention was measured as described in General methods for measuring conversion half-life. The results are presented in Table 2. All compounds of the invention had a conversion half-life of 3.6 days or more. The compounds of the invention are associated with a surprisingly high conversion half-life.

TABLE 2

| Conversion half-life | |
|---|---|
| Compound | Conversion half-life [days] |
| Chem. 14 | 4.4 |
| Chem. 15 | 4.2 |
| Chem. 16 | 4.7 |
| Chem. 17 | 4.4 |
| Chem. 18 | 4.8 |
| Chem. 19 | 3.7 |
| Chem. 20 | 5.6 |
| Chem. 21 | 3.9 |
| Chem. 22 | 7.2 |
| Chem. 23 | 5.5 |
| Chem. 24 | 6.7 |
| Chem. 25 | 6.1 |
| Chem. 26 | 4.9 |
| Chem. 27 | 4.7 |
| Chem. 28 | 6.9 |
| Chem. 29 | 9.1 |
| Chem. 30 | 8.4 |
| Chem. 31 | 8.0 |
| Chem. 32 | 3.6 |
| Chem. 33 | 3.8 |
| Chem. 34 | 3.7 |
| Chem. 35 | 0.7 |
| Chem. 36 | 24.1 |
| Chem. 37 | 2.5 |

General Methods for Measuring Terminal Half-Life

The assay was performed to investigate the terminal half-life of a drug administered in its free form or to investigate the observed terminal half-life for a drug (i.e. a parent drug) administered as a prodrug. The terminal half-life was investigated in mini-pigs.

Three (3) Göttingen minipigs (app. 25 kg) was equipped with two central catheters. One catheter was used for dosing i.v. with e.g. 10 nmol/kg (0.05 ml/kg) of the test compound formulated in a suitable formulation such as phosphate, propylene glycol and polysorbate, pH 7.4, and flushed with saline. After dosing, blood samples (0.8 ml) were taken via the second catheter at predetermined time points (0-3 weeks). The samples were centrifuged and 0.2 ml plasma were used for bioanalysis.

Bioanalysis was carried out as follows: plasma samples were crashed by protein precipitation and analysed by turboflow LCMS. Calibrators were prepared by spiking blank plasma from the relevant species with the test compound, typically in the range from 0.5 to 500 nM. Calibrators, plasma blanks and study samples were precipitated with 3 volumes of ethanol followed by centrifugation at 6300 rpm at 4° C. for 30 minutes. In matrixes where a higher background interference was observed a second precipitation with acetonitrile in ratio 1:1 was carried out. The supernatants were diluted with water containing 1% formic acid in ratio 1:2 (or 1:1). The samples were analysed by turboflow LCMS using Cyclone turboflow column (TurboFlow Cyclone 0.5×50 mm, Thermo Fischer Scientific), at room temperature and an Aeris Peptide 3.6 μm XB-C18 analytical column (2.1×50 mm, Phenomenex) at 60° C. A gradient elution was used using mobile phase A (consisting of milli-Q water with 1% formic acid and 5% methanol/acetonitrile (50/50)) and mobile phase B (consisting of methanol/acetonitrile (50/50) with 1% formic acid and 5% milli-Q water). A QExactive Plus mass spectrometer was used as a detector in single ion monitoring mode. Linear calibration curves (weighed 1/x2) was used for calculating the concentration in the plasma samples.

Plasma concentration (vs time) profiles of the test compounds were evaluated and standard pharmacokinetic parameters were estimated by non-compartmental analysis (NCA) using WinNonlin Phoenix 64 (version 8.10, CERTARA). The terminal half-life and/or the observed terminal half-life was estimated using the best fit model optimizing the $R^2$. A model was built to fit the data using NMLE add on to Phoenix 64 (version 8.10, CERTARA).

Example 26

The terminal half-life and/or the observed terminal half-life was measured as described in

| Compound | Conversion half-life [days] |
|---|---|
| Chem. 14 | 4.4 |
| Chem. 15 | 4.2 |
| Chem. 16 | 4.7 |
| Chem. 17 | 4.4 |
| Chem. 18 | 4.8 |
| Chem. 19 | 3.7 |
| Chem. 20 | 5.6 |
| Chem. 21 | 3.9 |
| Chem. 22 | 7.2 |
| Chem. 23 | 5.5 |
| Chem. 24 | 6.7 |
| Chem. 25 | 6.1 |
| Chem. 26 | 4.9 |
| Chem. 27 | 4.7 |
| Chem. 28 | 6.9 |
| Chem. 29 | 9.1 |
| Chem. 30 | 8.4 |
| Chem. 31 | 8.0 |
| Chem. 32 | 3.6 |
| Chem. 33 | 3.8 |
| Chem. 34 | 3.7 |
| Chem. 35 | 0.7 |
| Chem. 36 | 24.1 |
| Chem. 37 | 2.5 |

General methods for measuring terminal half-life. The terminal half-life of semaglutide administered in its free form was 69 hours in minipigs. The observed terminal half-life of four compounds of the invention as well as a reference compounds is presented in Table 3. The observed terminal half-life (of released semaglutide) of the compounds of the invention was at least 100 hours. The compounds of the invention are associated with a surprisingly high observed terminal half-life, and this constitutes proof of concept for prodrug technology claimed herein.

TABLE 3

| Observed terminal half-life in minipigs | |
|---|---|
| Compound | Observed terminal half-life [hours] |
| Test 1 | 100 |
| Test 2 | 101 |
| Test 3 | 105 |

TABLE 3-continued

| Observed terminal half-life in minipigs | |
|---|---|
| Compound | Observed terminal half-life [hours] |
| Test 4 | 109 |
| Chem. 37 | 78 |

General Methods for Measuring Oral Bioavailability

This assay was performed to measure the oral bioavailability of a compound. The assay determined the exposure of test compound following oral administration in Beagle dogs as described by relevant pharmacokinetic parameters and plasma concentration curves.

Preparation of tablets for oral administration: tablets containing test compound used for the assay described herein were immediate release SNAC-based tablets. The test compound was spray-dried as neutral sodium salt (pH 7-8). Dry granulation was carried out by roller compaction on a Gerteis MINI-PACTOR. Tablets containing 3 mg test compound, 300 mg sodium N-(8-(2-hydroxybenzoyl)amino) caprylate (SNAC) and 7.7 mg magnesium stearate were produced on at Kilian Style One using 7.2×12 mm punches.

Determination of the absorption following oral administration: eight (8) male Beagle dogs, 1 to 5 years of age and weighing approximately 10-12 kg at the start of the studies, were used. The dogs were group-housed in pens (12 hours light:12 hours dark), and fed individually and restrictedly once daily with Royal Canin Medium Adult dog (Royal Canin Products, China Branch, or Brogaarden A/S, Denmark). Exercise and group social were permitted daily, whenever possible. The dogs were used for repeated pharmacokinetic studies with a suitable wash-out period between successive dosing. An appropriate acclimatisation period was given prior to initiation of the first pharmacokinetic study. All handling, dosing and blood sampling of the animals were performed by trained and skilled staff. Before the studies the dogs were fasted overnight and from 0 to 4 h after dosing. Besides, the dogs were restricted to water 1 hour before dosing until 4 hours after dosing, but otherwise had ad libitum access to water during the whole period.

Tablets containing the test compound were administered in the following manner: 10 min prior to tablet administration the dogs were dosed subcutaneously with approximately 3 nmol/kg of SEQ ID NO: 4. The tablets were placed in the back of the mouth of the dog to prevent chewing. The mouth was then closed and 10 mL or 50 mL of tap water was given by a syringe to facilitate swallowing of the tablet. Blood was sampled at predefined time points for up till 336 hours after dosing to adequately cover the full plasma concentration-time absorption profile of the prodrug. For each blood sampling time point approximately 1.2 mL of whole blood was collected in a 1.5 mL EDTA coated tube, and the tube was gently turned to allowing mixing of the sample with the EDTA. Then, the blood samples was kept on ice until centrifugation (4 min, 4° C., 4000 rpm). Plasma was pipetted into Micronic tubes on dry ice, and kept at −20° C. until analysis. Blood samples were taken as appropriate, for example from a venflon in the cephalic vein in the front leg for the first 2 hours and then with syringe from the jugular vein for the rest of the time points (the first few drops were allowed to drain from the venflon to avoid heparin saline from the venflon in the sample).

Bioanalysis was carried out as follows: plasma concentrations of test compound were assayed by plasma protein precipitation and analysed by liquid chromatography-mass spectrometry (LC-MS). Calibrators were prepared by spiking blank dog plasma with analytes to reach the final concentrations in the range typically from 2 to 200 nM. Calibrators, plasma blanks or study samples were prepared for LC-MS by protein precipitation by adding 3 volumes of ethanol followed by centrifugation at 4000 rpm at 4° C. for 1 h. The supernatant was diluted with 2 volumes of Milli-Q water containing 1% formic acid before injection on the LC-MS system. The system used was a Transcend II Interface Module SRD3200 system from Thermo Scientific (Waltham, MA, USA) coupled to a Orbitrap Exploris 240 mass spectrometer from Thermo Scientific. The LC was equipped with a Cyclone column (CH-953288, Thermo Scientific) as the first dimensional trapping column and Poroshell 120 SB-C18 2.7 μm as the analytical column (2.1×50 mm from Agilent, Santa Clara, CA, USA). The mobile phase composition of the loading pump is as below: mobile phase A consists of 95% milli-Q water, 2.5% acetonitrile, 2.5% methanol and 0.1% formic acid; mobile phase B consists of 47.5% acetonitrile, 47.5% methanol, 5% milli-Q water, and 0.1% formic acid. The analyte of interest was loaded from the Turbo flow column at 30% B to the second dimensional analytical column. A gradient elution was conducted at the elution pump using mobile phase A (95% milli-Q water, 2.5% acetonitrile, 2.5% methanol and 0.1% formic acid) and mobile phase B (47.5% acetonitrile, 47.5% methanol, 5% milli-Q water, and 0.1% formic acid) with a ramping gradient of 0% mobile phase B to 70% mobile phase B in 0.25 minute and from 70% mobile phase B to 80% mobile phase B in 1.17 min, and then from 80% mobile phase B to 95% mobile phase B in 1.17 min. The Orbitrap Exploris 240 was operating in positive ionization mode with the parallel reaction monitoring (PRM) scan mode. Linear calibration curves (weighting 1/x2) were used for calculating the test compound concentrations in the plasma samples to determine maximal plasma concentration (Cmax). Quality control samples for analytes were included. The deviation between nominal and calculated concentration in the calibrators and quality control samples were below 15% and the LLOQ sample was below 20%. The plasma concentration (vs time) profile of the test compound was evaluated and standard pharmacokinetic parameters were estimated by non-compartmental analysis (NCA) using WinNonlin Phoenix 64 (version 8.10, CERTARA). Results were reported as dose normalised plasma concentration (vs time) profiles as well as dose-corrected maximum plasma concentration (Cmax/Dose) and dose-corrected area under curve (AUC/Dose).

Example 27

The oral bioavailability was determined as described in General methods for measuring oral bioavailability. Relevant pharmacokinetic parameters of four compounds of the invention as well as a reference compounds is presented in Table 4. The compounds of the invention are associated with a surprisingly high Cmax/Dose. Dose normalised plasma concentration (vs time) profiles of four compounds of the invention as well as a reference compounds is presented in FIG. 1. The compounds of the invention are associated with a surprisingly high exposure as determined by the dose normalised plasma concentration profiles. The compounds of the invention are associated with a surprisingly high oral bioavailability.

TABLE 4

| Pharmacokinetic parameters following oral administration in Beagle dogs | | |
|---|---|---|
| Compound | Cmax/Dose [kg/L] | AUC/Dose [kg*hr/L] |
| Test 1 | 0.21 | 12.1 |
| Test 2 | 0.30 | 15.9 |
| Test 3 | 0.39 | 19.5 |
| Test 4 | 0.49 | 22.1 |
| Chem. 37 | 0.10 | 1.6 |

The invention claimed is:

1. A compound comprising A-Z (Formula I), wherein Z comprises a GLP-1 polypeptide;

wherein A is of Formula II:

(Formula II)

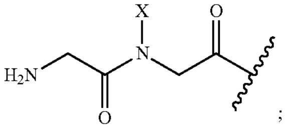

;

wherein X is of Formula III:

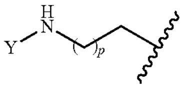

(Formula III);

wherein p is 1-5; and wherein Y comprises a lipophilic moiety comprising a distal carboxylic acid;

or a pharmaceutical acceptable salt, ester or amide thereof.

2. The compound according to claim 1, wherein the N-terminal amino group of the GLP-1 polypeptide is linked to A via an amide bond.

3. The compound according to claim 1, wherein the N-terminal residue of the GLP-1 polypeptide is His.

4. The compound according to claim 1, wherein the GLP-1 polypeptide is a GLP-1 analogue comprising maximum of 2 amino acid changes as compared to GLP-1(7-37) (SEQ ID NO: 1).

5. The compound according to claim 1, wherein Z is semaglutide.

6. The compound according to claim 1, wherein the lipophilic moiety comprising a distal carboxylic acid is a moiety selected from the group consisting of (Chem. 12)

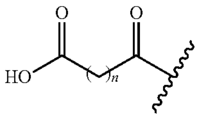

, wherein n is 12, 14, 16 or 18; and (Chem. 13)

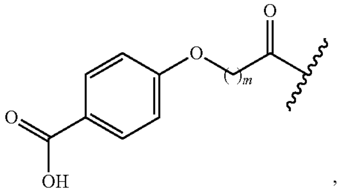

, wherein m is 9 or 10.

7. The compound according to claim 6, wherein Y is (Chem. 6)

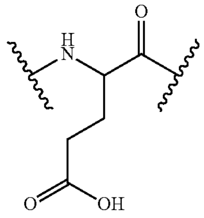

or (Chem. 7)

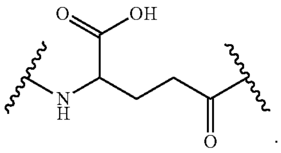

.

8. The compound according to claim 1, wherein Y is $A_5$-$A_4$-$A_3$-$A_2$-$A_1$- (Formula IV);

wherein $A_1$, $A_2$ and $A_3$ are each absent or individually selected from the group consisting of (Chem. 8)

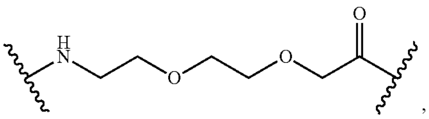

, (Chem. 9)

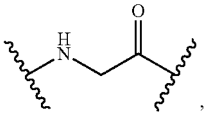

,

-continued (Chem. 10)

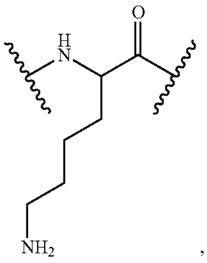

, and (Chem. 11)

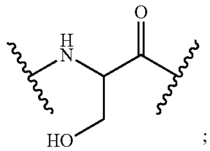

; wherein $A_4$ is (Chem. 6)

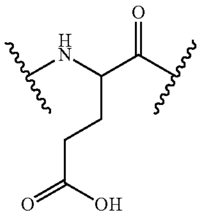

or (Chem. 7)

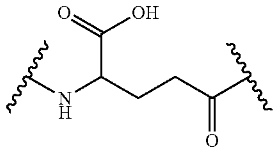

and wherein $A_5$ is (Chem. 12)

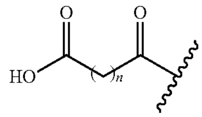

, wherein n is 12, 14, 16 or 18; or (Chem. 13)

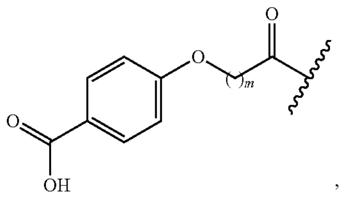

, wherein m is 9 or 10.

9. The compound according to claim 8, wherein the residues $A_5$, $A_4$, $A_3$, $A_2$, and $A_1$ are interconnected via amide bonds.

10. The compound according to claim 1, wherein the compound is a prodrug and Z is a parent drug, and wherein the prodrug to drug conversion half-life, determined in vitro at 37° C. and pH 7.4, is at least 3.0 days.

11. The compound according to claim 1, wherein the compound is a prodrug and Z is a parent drug, and wherein the observed terminal half-life of the parent drug, determined upon administration of the prodrug in mini-pigs, is >80 hours.

12. The compound according to claim 1, wherein the compound is selected from the group consisting of (Chem. 14)

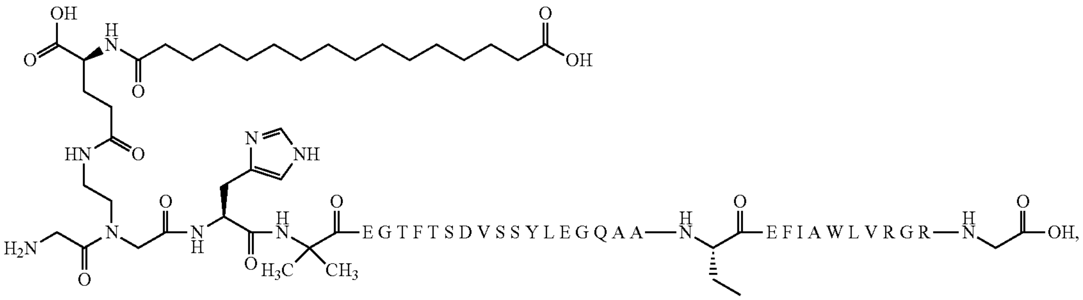

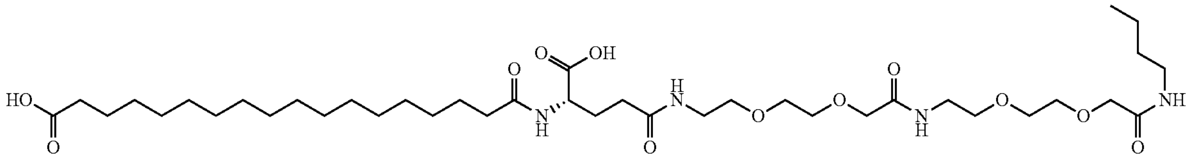

-continued
(Chem. 15)
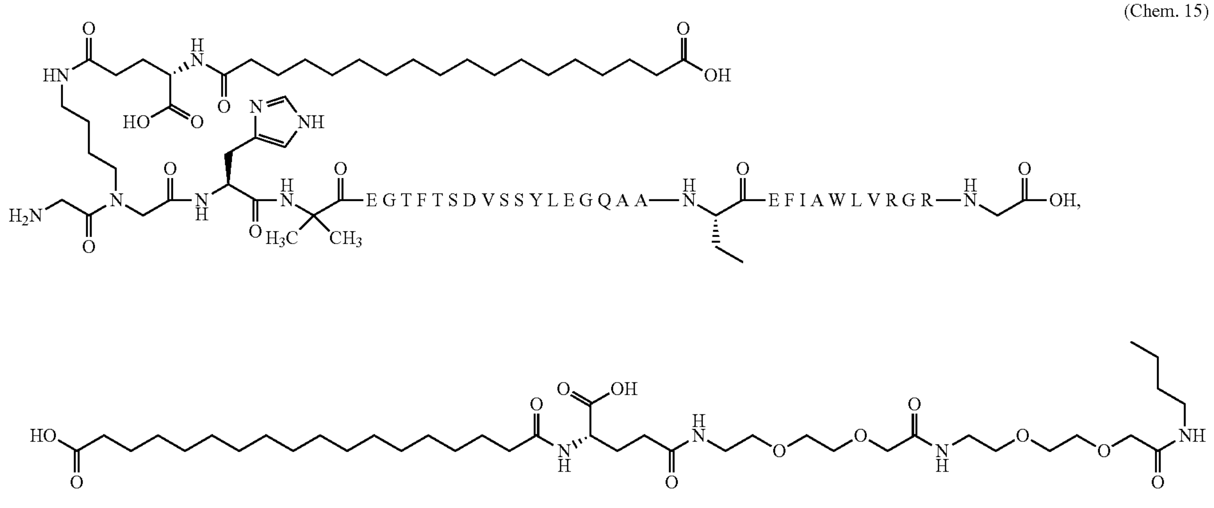
(Chem. 16)
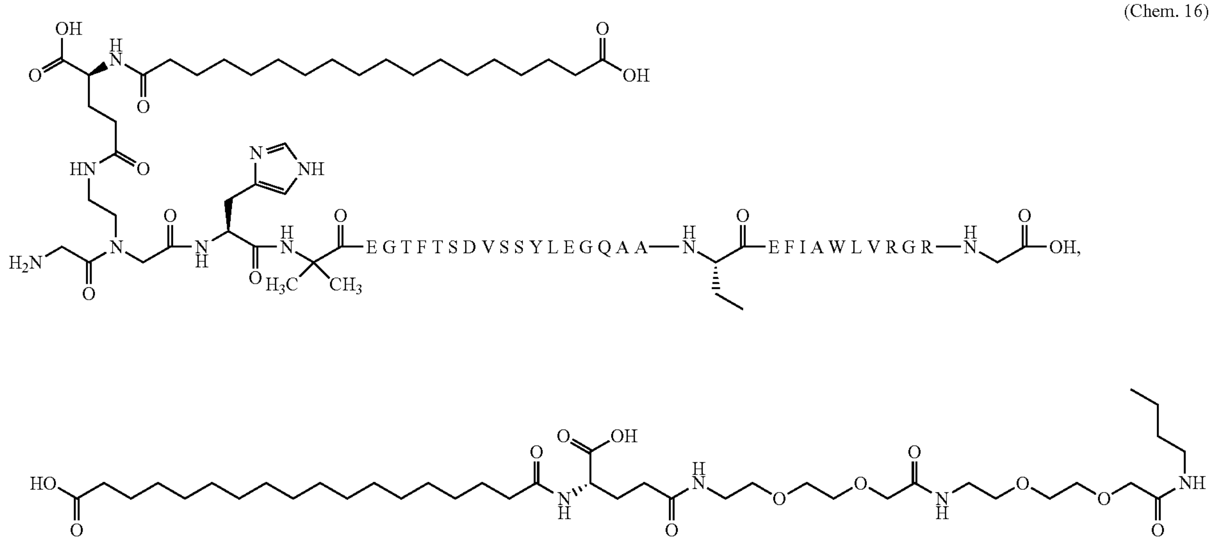
(Chem. 17)
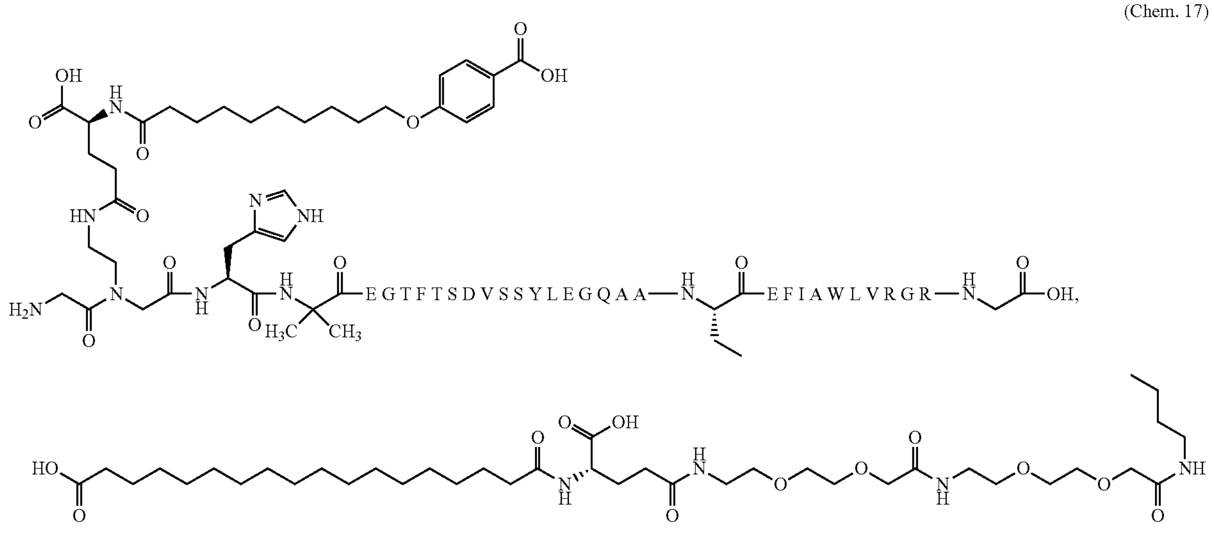

-continued
(Chem. 18)
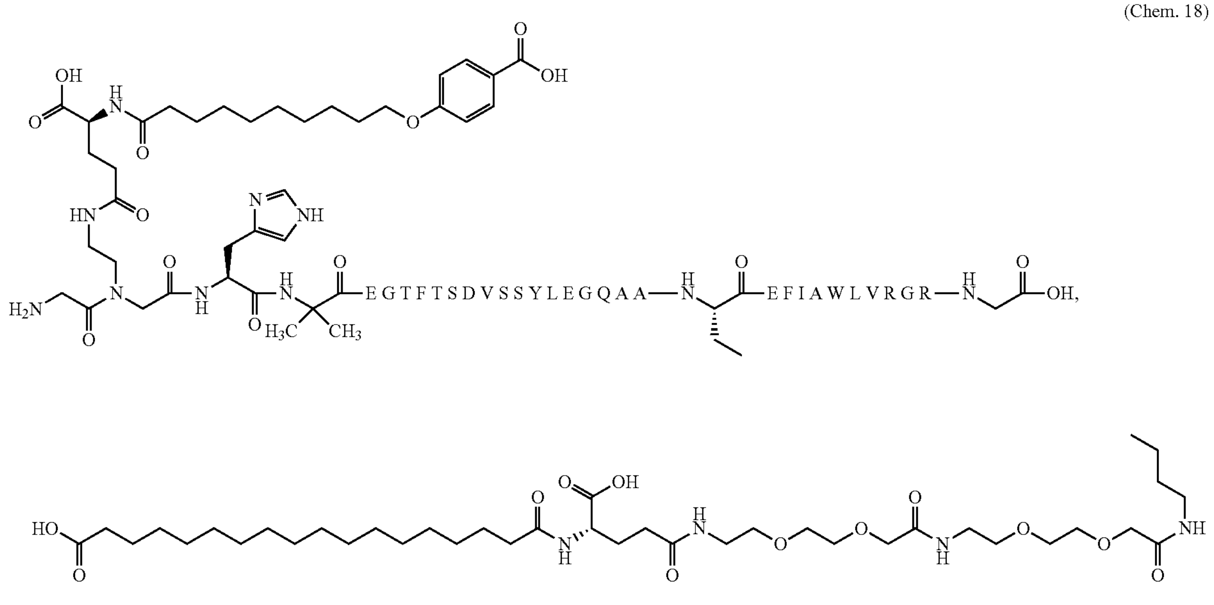
(Chem. 19)
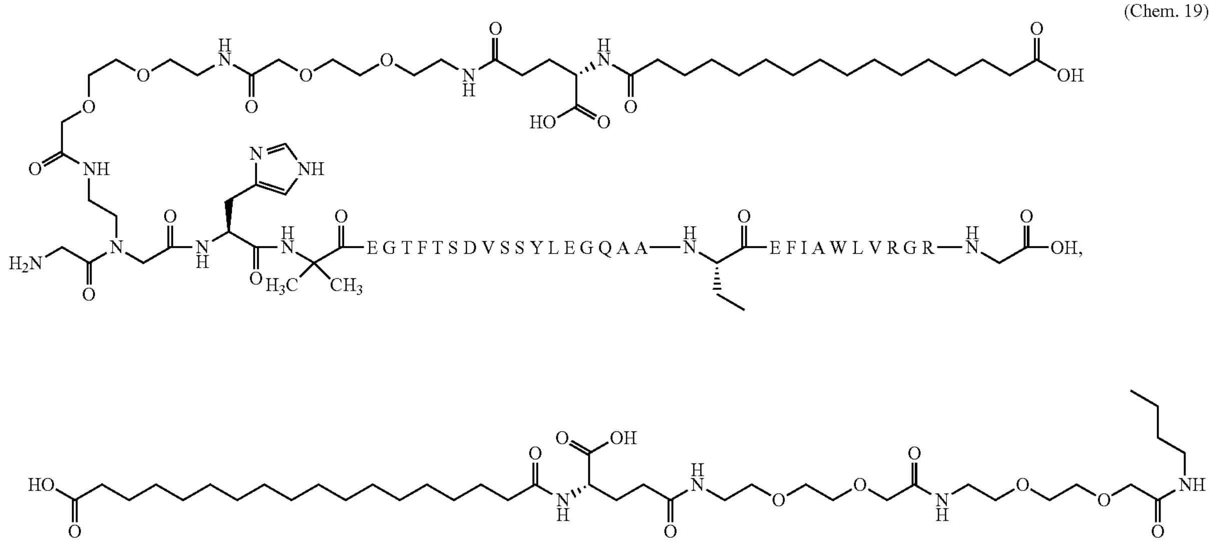
(Chem. 20)
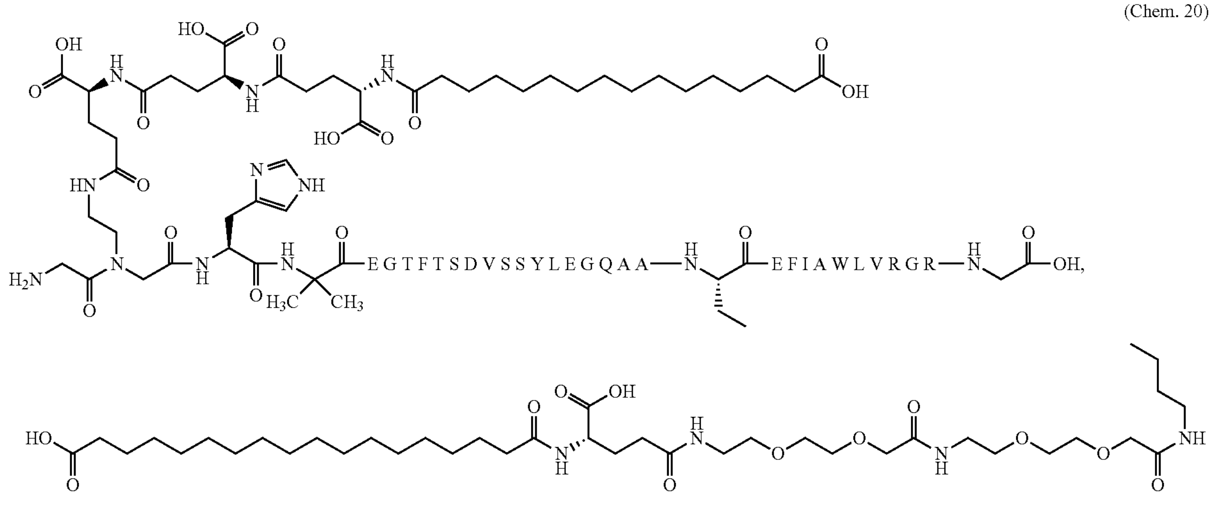

-continued
(Chem. 21)
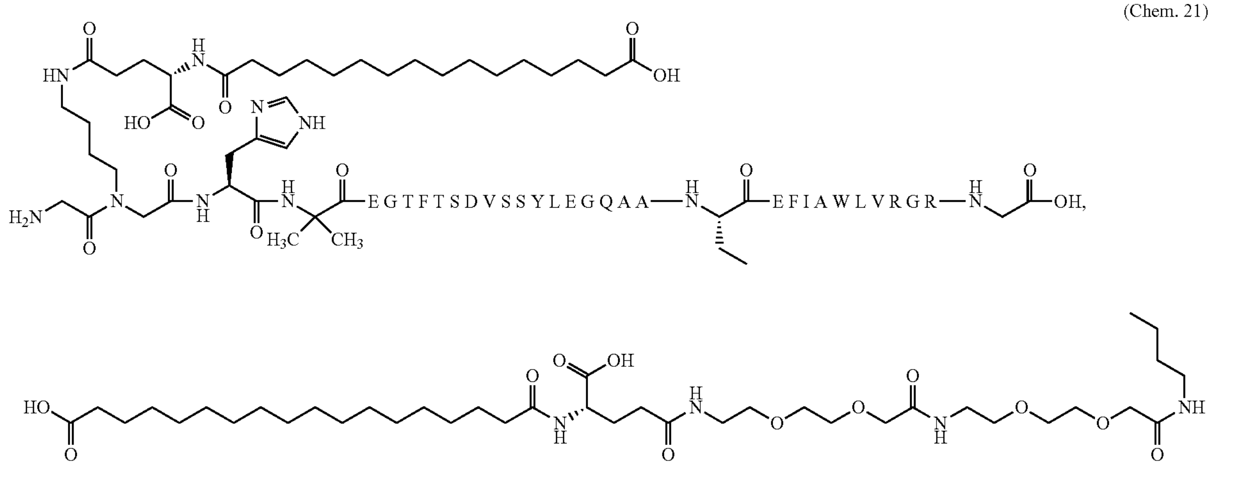
(Chem. 22)
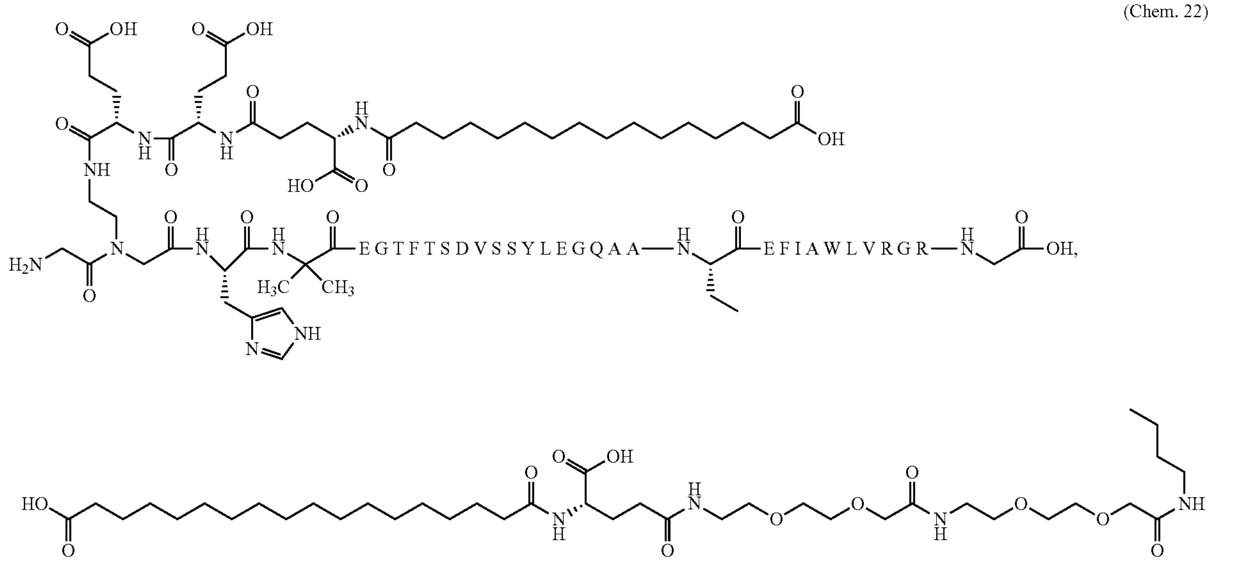
(Chem. 23)
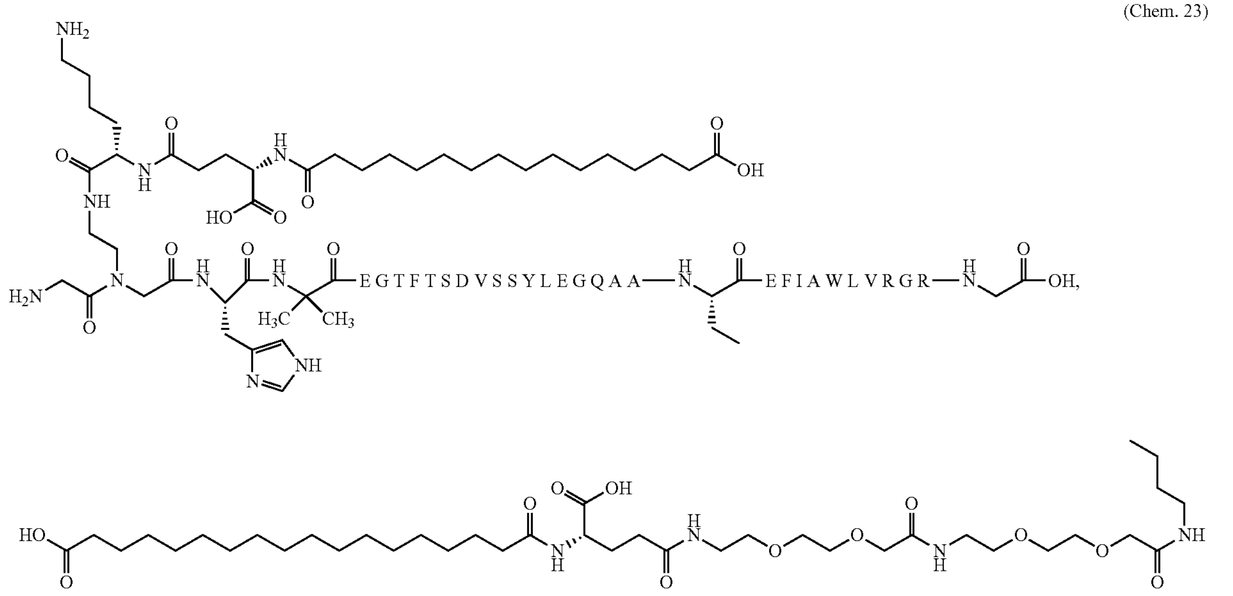

-continued
(Chem. 24)
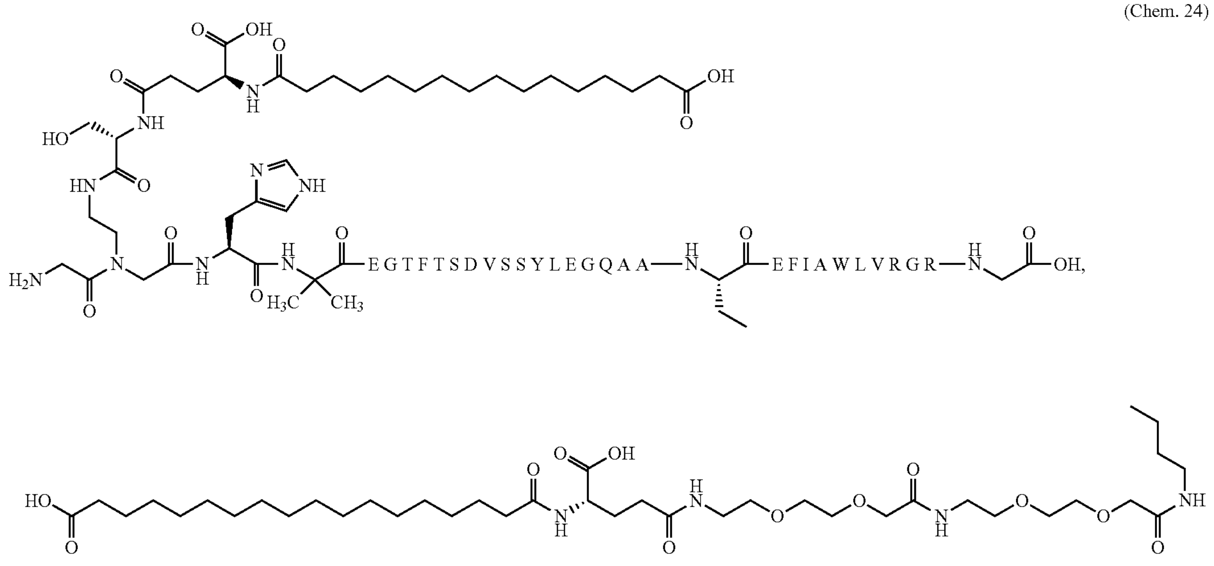
(Chem. 25)
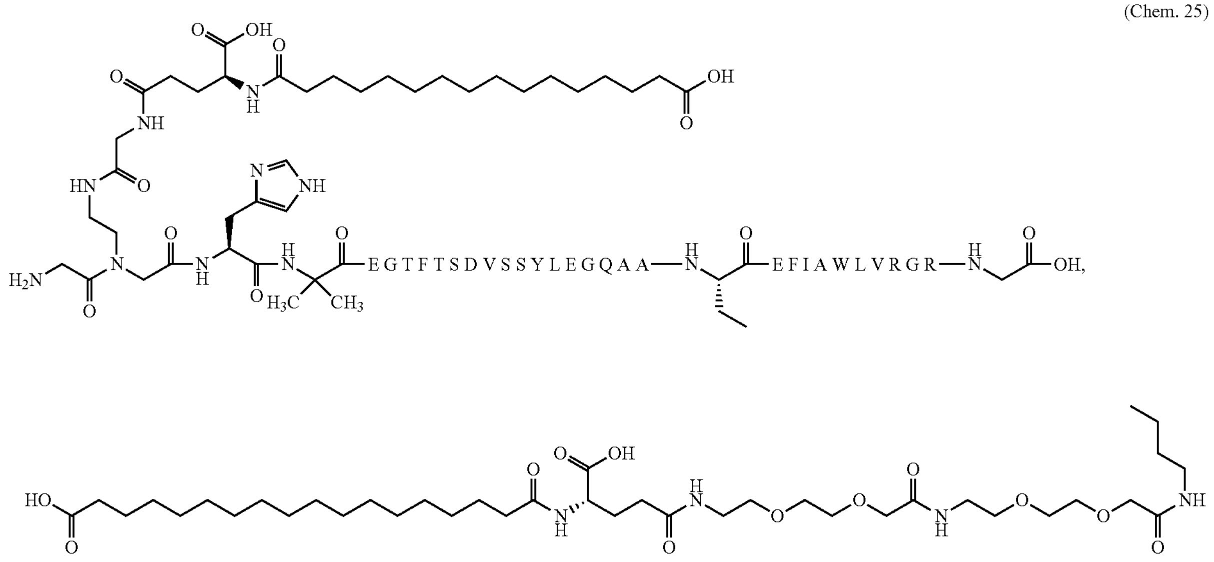
(Chem. 26)
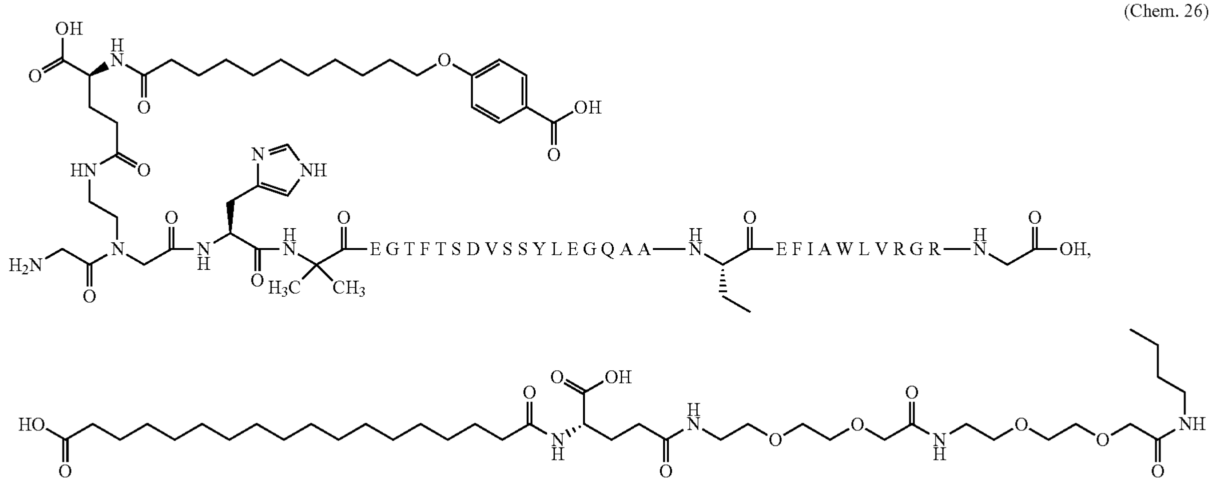

-continued
(Chem. 27)
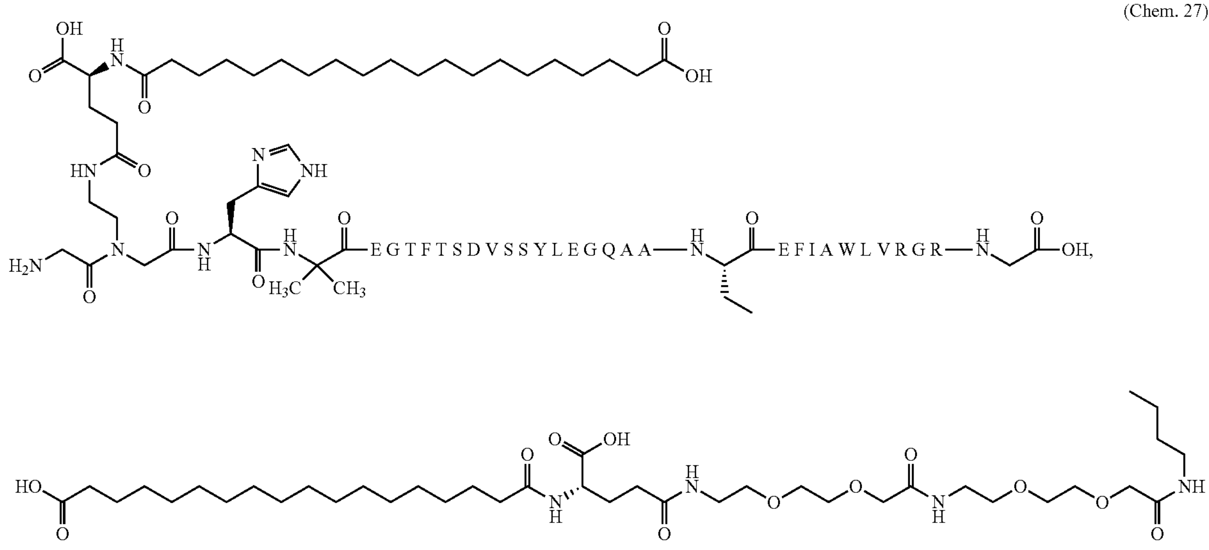
(Chem. 28)
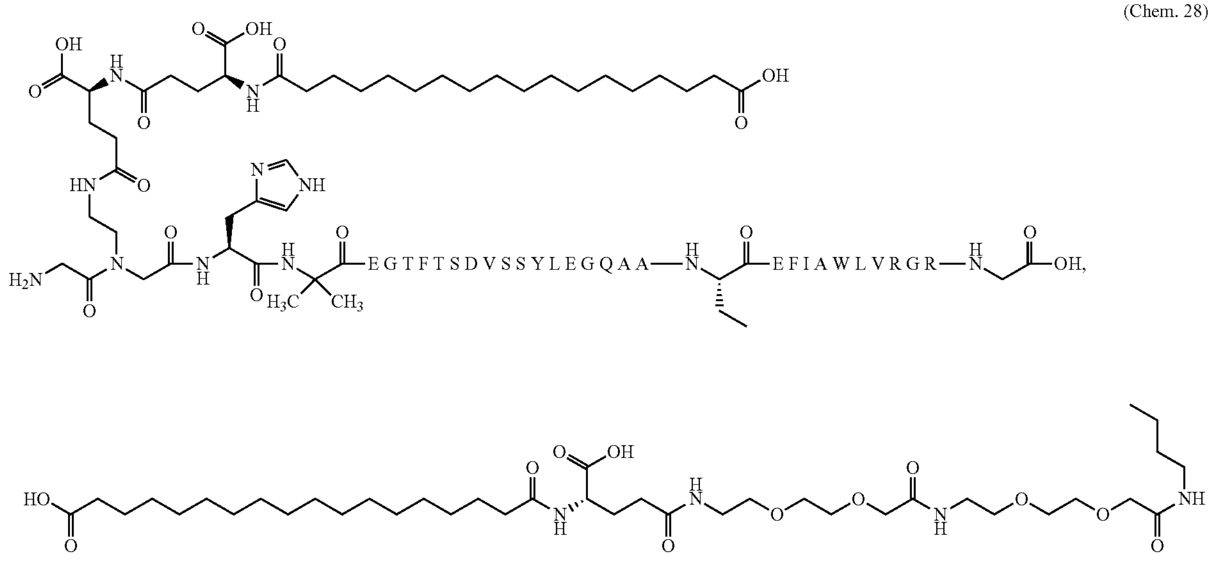
(Chem. 29)
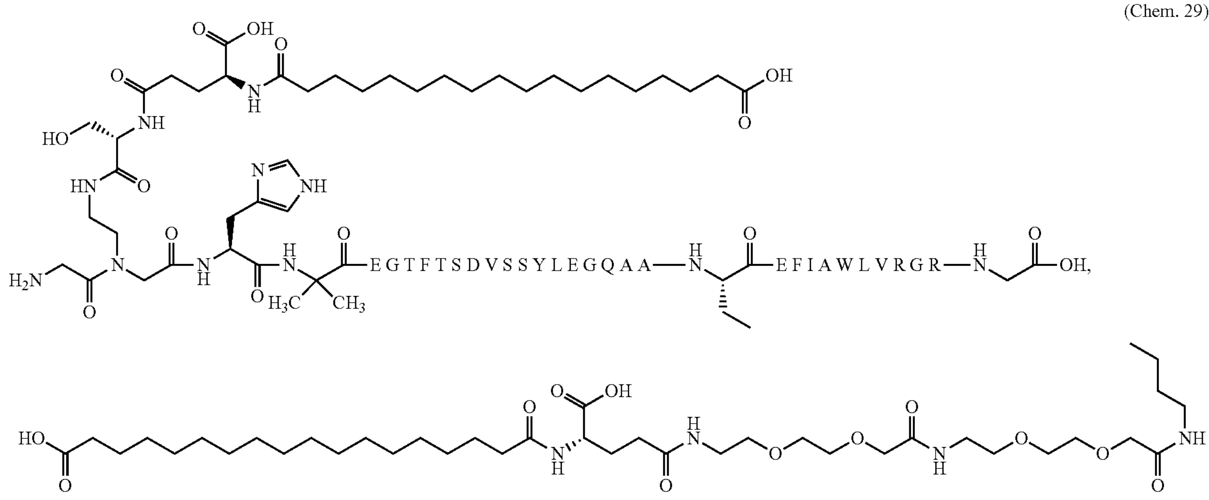

-continued
(Chem. 30)
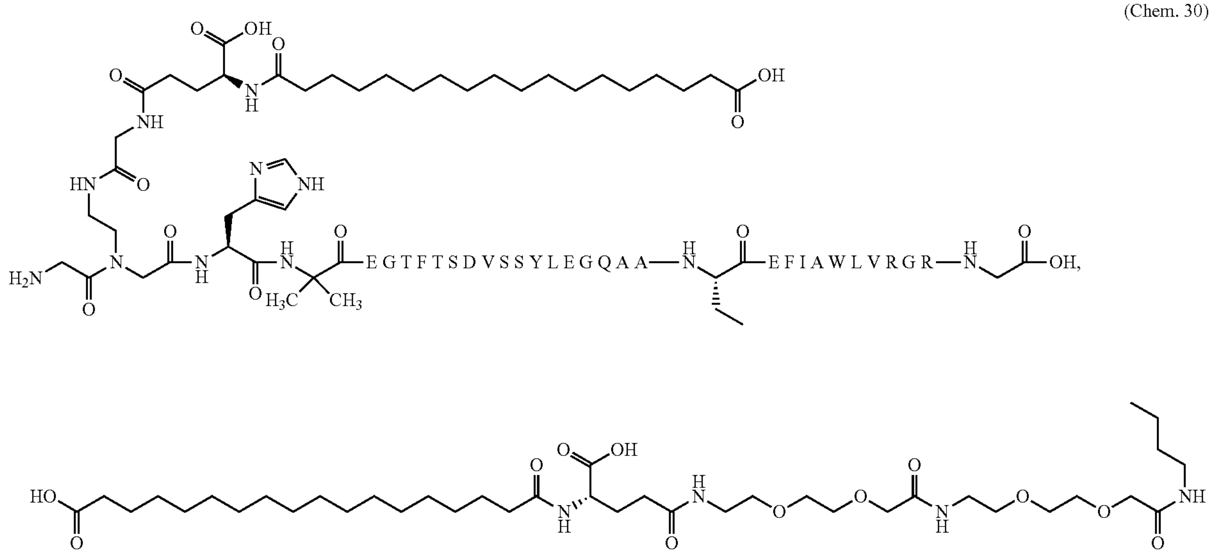
(Chem. 31)
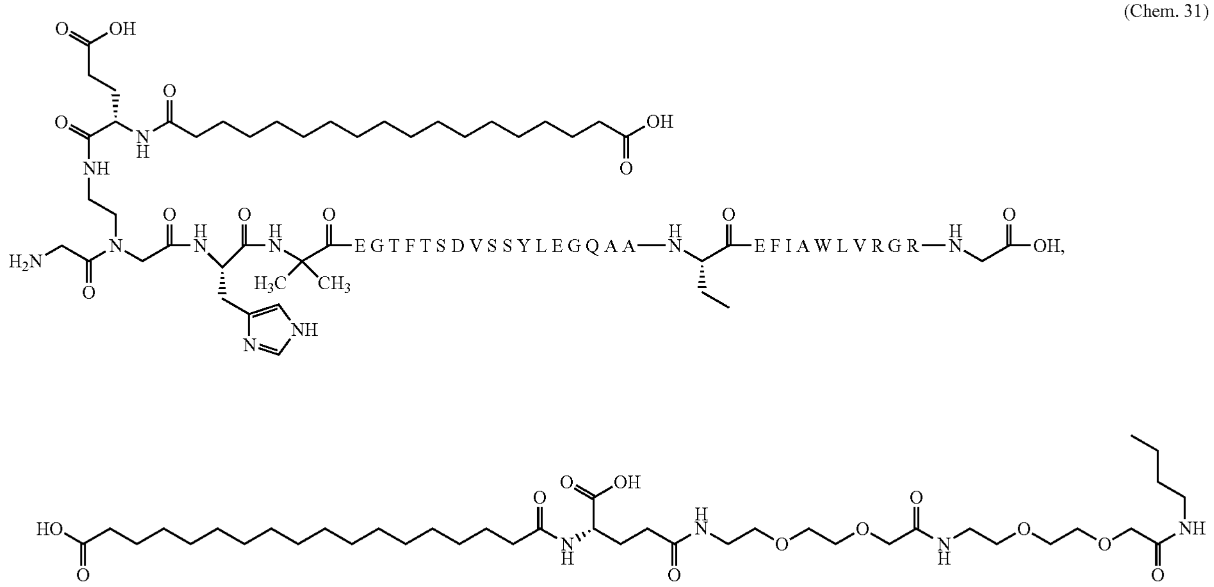
(Chem. 32)
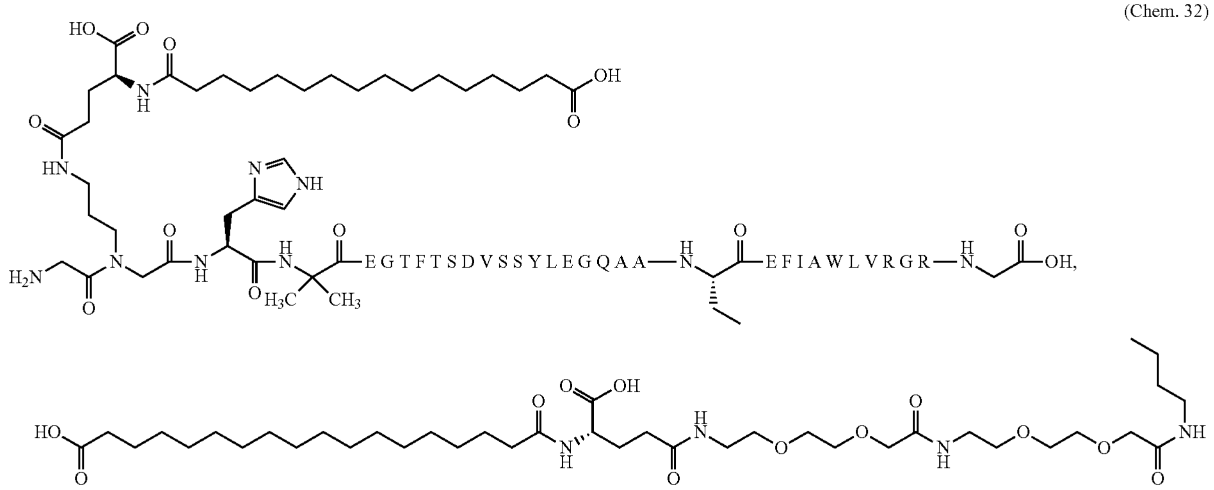

-continued (Chem. 33)

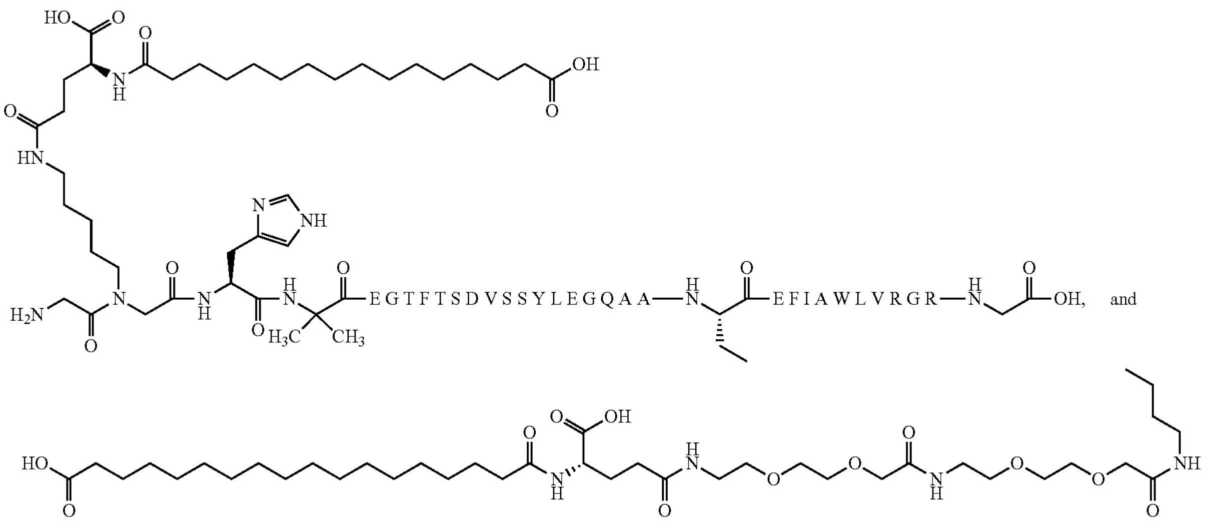

and (Chem. 34)

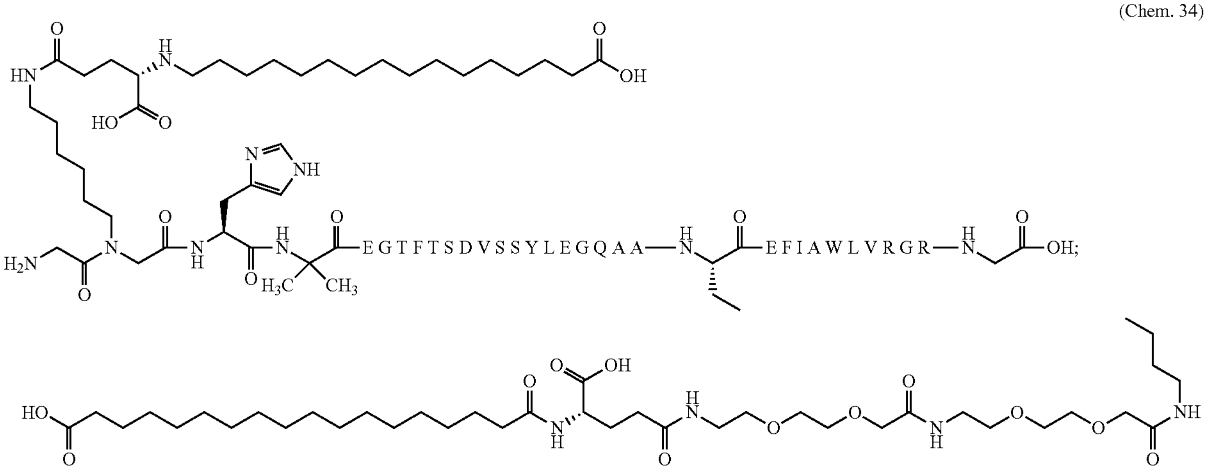

or a pharmaceutical acceptable salt, ester or amide thereof.

13. A method for treating type 2 diabetes, comprising administering the compound according to claim 1 to a subject in need thereof.

14. A method for treating type 2 diabetes, comprising administering the compound according to claim 12 to a subject in need thereof.

15. A method for reducing body weight, comprising administering the compound according to claim 1 to a subject in need thereof.

16. The method according to claim 15, wherein the subject is suffering from obesity.

17. A method for reducing body weight, comprising administering the compound according to claim 12 to a subject in need thereof.

18. The method according to claim 17, wherein the subject is suffering from obesity.

19. A method for treating a disease of the liver, comprising administering the compound according to claim 1 to a subject in need thereof, wherein the disease of the liver is non-alcoholic fatty liver disease (NAFLD) or non-alcoholic steatohepatitis (NASH).

20. A method for treating a disease of the liver, comprising administering the compound according to claim 12 to a subject in need thereof, wherein the disease of the liver is non-alcoholic fatty liver disease (NAFLD) or non-alcoholic steatohepatitis (NASH).

21. A method for treating cardiovascular disease, comprising administering the compound according to claim 1 to a subject in need thereof, wherein the cardiovascular disease is peripheral arterial disease.

22. A method for treating cardiovascular disease, comprising administering the compound according to claim 12 to a subject in need thereof, wherein the cardiovascular disease is peripheral arterial disease.

23. A method for treating a kidney disease, comprising administering the compound according to claim 1 to a subject in need thereof, wherein the kidney disease is chronic kidney disease (CKD) or diabetic kidney disease (DKD).

24. A method for treating a kidney disease, comprising administering the compound according to claim 12 to a subject in need thereof, wherein the kidney disease is chronic kidney disease (CKD) or diabetic kidney disease (DKD).

* * * * *

SEQUENCE LISTING

```
<160> NUMBER OF SEQ ID NOS: 4

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 2
<211> LENGTH: 31
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (2)..(2)
<223> OTHER INFORMATION: Aib

<400> SEQUENCE: 2

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 3
<211> LENGTH: 33
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (2)..(2)
<223> OTHER INFORMATION: Modified G
<220> FEATURE:
<221> NAME/KEY: MISC_FEATURE
<222> LOCATION: (4)..(4)
<223> OTHER INFORMATION: Aib

<400> SEQUENCE: 3

Gly Xaa His Xaa Glu Gly Thr Phe Thr Ser Asp Val Ser Ser Tyr Leu
1               5                   10                  15

Glu Gly Gln Ala Ala Lys Glu Phe Ile Ala Trp Leu Val Arg Gly Arg
            20                  25                  30

Gly


<210> SEQ ID NO 4
<211> LENGTH: 29
<212> TYPE: PRT
```

-continued

```
<213> ORGANISM: Homo sapiens

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```